United States Patent [19]

Göschke et al.

[11] Patent Number: 4,476,132
[45] Date of Patent: Oct. 9, 1984

[54] ACYLQUINOLINONE DERIVATIVES, AND ANTIALLERGIC PREPARATIONS AND METHODS OF INHIBITING ALLERGIC REACTIONS USING THEM

[75] Inventors: Richard Göschke, Bottmingen; Pier G. Ferrini, Binningen; Alfred Sallmann, Bottmingen, all of Switzerland

[73] Assignee: Ciba-Geigy Corporation, Ardsley, N.Y.

[21] Appl. No.: 360,016

[22] Filed: Mar. 19, 1982

[30] Foreign Application Priority Data

Mar. 24, 1981 [CH] Switzerland ............... 1986/81

[51] Int. Cl.$^3$ .................. A61K 31/47; C07D 215/22
[52] U.S. Cl. ........................... 424/258; 546/155; 546/156; 544/94; 560/19; 560/44; 562/458; 564/199; 564/414; 548/485; 548/486
[58] Field of Search ............... 546/156, 155; 424/258

[56] References Cited

U.S. PATENT DOCUMENTS

| | | | |
|---|---|---|---|
| 3,496,184 | 2/1970 | Mizzoni et al. | 544/156 |
| 3,830,817 | 8/1974 | Narayanan | 424/258 X |
| 4,086,349 | 4/1978 | Morinaka et al. | 424/258 |
| 4,119,720 | 10/1978 | Hardtmann | 424/258 |
| 4,186,201 | 1/1980 | Erickson | 424/258 |
| 4,187,309 | 2/1980 | Hardtmann | 424/258 |
| 4,190,659 | 2/1980 | Hardtmann | 424/258 |
| 4,223,137 | 9/1980 | Yoshizaki et al. | 544/128 |

FOREIGN PATENT DOCUMENTS

| | | | |
|---|---|---|---|
| 2103805 | 8/1971 | Fed. Rep. of Germany | 424/258 |
| 0012872 | 2/1978 | Japan | 424/258 |
| 830832 | 3/1960 | United Kingdom . | |
| 1013224 | 12/1965 | United Kingdom . | |
| 1334705 | 10/1973 | United Kingdom . | |
| 1374463 | 11/1974 | United Kingdom . | |

OTHER PUBLICATIONS

Hall et al., J. Med. Chem., 17(7), pp. 685–690 (1974).
Mizzoni et al., Chemical Abstracts, vol. 73, 87757f (1970).
Hermans et al., Chemical Abstracts, vol. 74, 99901g (1971).
Murakami et al., Chemical Abstracts, vol. 80, 70803q (1974).
Kametani et al., Chemical Abstracts, vol. 90, 22775s (1979).
Kigasawa et al. Chemical Abstracts, vol. 92, 128747r (1980).
Koga et al., Chemical Abstracts, vol. 93, 198382n (1980).
Erickson et al., J. Med. Chem. 21 (9), pp. 984–988 (1978).
Germany 1,908,548, 11/05/70, Abstract.

*Primary Examiner*—Donald G. Daus
*Assistant Examiner*—Diana G. Rivers
*Attorney, Agent, or Firm*—Michael W. Glynn; Irving N. Feit

[57] ABSTRACT

Quinolinone derivatives of the formula (I)

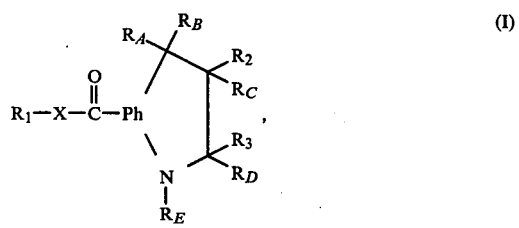

in which X represents oxy or a direct bond, $R_1$ represents an aliphatic, cycloaliphatic, aromatic, araliphatic, heterocyclic or heterocyclic-aliphatic radical or hydrogen, Ph represents an optionally additionally substituted 1,2-phenylene radical containing the group $R_1$—X—C(O)—, and one of the radicals $R_2$ and $R_3$ represents an optionally esterified or amidated carboxy group $R_4$ and the other represents hydrogen or an aliphatic radical or, in the case of a radical $R_3$, hydroxy, and in which either $R_A$ and $R_B$ together represent oxo, $R_C$ and $R_D$ together represent an additional bond, or, when $R_2$ represents a radical $R_4$, $R_C$ is hydrogen and $R_3$ and $R_D$ together represent oxo, and $R_E$ represents a radical $R_5$ which represents hydrogen or an aliphatic, cycloaliphatic, araliphatic heterocyclic-aliphatic radical, or $R_A$ represents an optionally etherified hydroxy group and $R_B$ together with $R_C$ and also $R_D$ together with $R_E$ represent an additional bond in each case, or, when $R_2$ represents a radical $R_4$, $R_B$ and $R_C$ together represent an additional bond and $R_3$ and $R_D$ together represent oxo and $R_E$ represents a radical $R_5$, and their salts, have antiallergic properties. They are manufactured, for example, by subjecting a compound of the formula (IV)

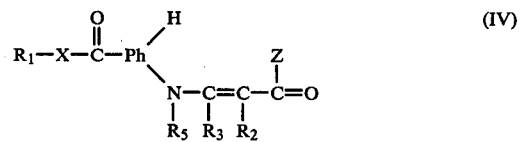

in which Z represents a removable radical, or a tautomer and/or salt thereof, to intramolecular cyclisation.

12 Claims, No Drawings

ACYLQUINOLINONE DERIVATIVES, AND ANTIALLERGIC PREPARATIONS AND METHODS OF INHIBITING ALLERGIC REACTIONS USING THEM

The invention relates to novel quinolinone derivatives of the formula (I)

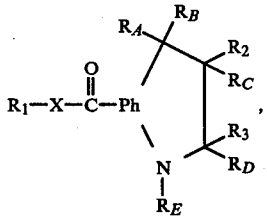

in which X represents oxy or a direct bond, $R_1$ represents an aliphatic, cycloaliphatic, aromatic, araliphatic, heterocyclic or heterocyclic-aliphatic radical or hydrogen, Ph represents an optionally additionally substituted 1,2-phenylene radical containing the group $R_1$—X—C-(O)—, and one of the radicals $R_2$ and $R_3$ represents an optionally esterified or amidated carboxy group $R_4$ and the other represents hydrogen or an aliphatic radical or, in the case of a radical $R_3$, hydroxy, and in which either $R_A$ and $R_B$ together represent oxo, $R_C$ and $R_D$ together represent an additional bond, or, when $R_2$ represents a radical $R_4$, $R_C$ is hydrogen and $R_3$ and $R_D$ together represent oxo, and $R_E$ represents a radical $R_5$ which represents hydrogen or an aliphatic, cycloaliphatic, araliphatic or heterocyclic-aliphatic radical, or $R_A$ represents an optionally etherified hydroxy group and $R_B$ together with $R_C$ and also $R_D$ together with $R_E$ represent an additional bond in each case, or, when $R_2$ represents a radical $R_4$, $R_B$ and $R_C$ together represent an additional bond and $R_3$ and $R_D$ together represent oxo and $R_E$ represents a radical $R_5$, and salts of salt-forming compounds of the formula (I), processes for their manufacture, pharmaceutical preparations containing compounds of the formula (I) or their salts, and the use of compounds of the formula (I) and their salts.

Aliphatic, cycloaliphatic, aromatic and araliphatic radicals are especially optionally substituted aliphatic, cycloaliphatic, aromatic or araliphatic hydrocarbon radicals, such as corresponding lower alkyl, lower alkenyl, lower alkynyl, cycloalkyl, phenyl or phenyl-lower alkyl. Substituents are, for example, hydroxy and/or lower alkoxy, and, in the case of radicals $R_1$, also lower alkylthio or phenylthio, lower alkanesulphinyl or benzenesulphinyl or lower alkanesulphonyl or benzenesulphonyl, also lower alkanoyloxy, hydroxy-lower alkoxy, lower alkoxy-lower alkoxy, hydroxy-lower alkoxy-lower alkoxy or lower alkoxy-lower alkoxy-lower alkoxy, and, in the case of radicals $R_5$, also di-lower alkylamino or lower alkylene- or aza-, oxa- or thia-lower alkylene-amino having from 5 to 7 ring members. Heterocyclyl in heterocyclic or heterocyclic-aliphatic radicals is especially monocyclic heterocyclyl of aromatic character having a hetero atom, such as oxygen, sulphur or nitrogen, as ring member, such as furyl, thienyl or pyridyl. In heterocyclic-aliphatic radicals the aliphatic moiety is, for example, a corresponding aliphatic hydrocarbon radical, especially lower alkyl.

There come into consideration as additional substituents of Ph, for example, lower alkyl, lower alkoxy, hydroxy and/or halogen.

Esterified carboxy is, for example, carboxy esterified by an aliphatic or araliphatic alcohol, such as an optionally substituted lower alkanol or phenyl-lower alkanol, such as corresponding lower alkoxy- or phenyl-lower alkoxy-carbonyl. Substituted lower alkoxycarbonyl is, for example, hydroxy-, lower alkoxy- or di-lower alkylamino- or lower alkyleneamino-, aza-lower alkyleneamino-, oxa-lower alkyleneamino- or thia-lower alkyleneamino-lower alkoxycarbonyl. Substituents of phenyl-lower alkoxycarbonyl are, for example, lower alkyl, lower alkoxy and/or halogen.

In amidated carboxy, the amino group represents, for example, amino that is optionally mono-substituted by hydroxy or mono- or di-substituted by aliphatic radicals, such as amino, hydroxyamino, mono- or di-lower alkylamino or 5- to 7-membered lower alkylene- or aza-, oxa- or thia-lower alkylene-amino.

Etherified hydroxy $R_A$ is, for example, lower alkoxy, lower alkenyloxy, lower alkoxy-lower alkoxy or di-lower alkylamino- or 5- to 7-membered lower alkylene- or aza-, oxo- or thia-lower alkylene-amino-lower alkoxy.

Hereinbefore and hereinafter, "lower" organic radicals and compounds are preferably understood as being those that have up to and including 7, especially up to and including 4, carbon atoms.

Lower alkyl represents, for example, methyl, ethyl, propyl, isopropyl, butyl, isobutyl, sec-butyl, tert-butyl, pentyl, hexyl or heptyl.

Lower alkenyl represents, for example, vinyl, 1-methylvinyl, 1-ethylvinyl, allyl or 2- or 3-methallyl.

Lower alkynyl represents, for example, ethynyl or prop-2-ynyl (propargyl).

Lower alkoxy and lower alkoxy in lower alkoxycarbonyl represent, for example, methoxy, ethoxy, propoxy, isopropoxy, butoxy, isobutoxy, sec-butoxy, tert-butoxy, pentyloxy, hexyloxy or heptyloxy.

Lower alkylthio is, for example, methylthio, ethylthio, propylthio, butylthio, pentylthio, hexylthio or heptylthio.

Hydroxy-lower alkyl is, for example, 2- and/or 3-hydroxy-lower alkyl, for example 2-hydroxyethyl, 3-hydroxypropyl or 2,3-dihydroxypropyl. Correspondingly, hydroxy-lower alkoxy and hydroxy-lower alkoxy in hydroxy-lower alkoxycarbonyl are especially 2- and/or 3-hydroxy-lower alkoxy, for example 2-hydroxyethoxy, 3-hydroxypropoxy or 2,3-dihydroxypropoxy, and hydroxy-lower alkoxy-lower alkoxy is especially ω-(ω-hydroxy-lower alkoxy)-lower alkoxy, for example 2-(2-hydroxyethoxy)-ethoxy.

Lower alkoxy-lower alkyl is, for example, 2- and/or 3-lower alkoxy-lower alkyl, for example 2-methoxyethyl, 2-ethoxyethyl or 3-methoxypropyl. Correspondingly, lower alkoxy-lower alkoxy and the same in lower alkoxy-lower alkoxycarbonyl are especially 2- and/or 3-lower alkoxy-lower alkoxy, for example 2-methoxyethoxy, 2-ethoxyethoxy or 3-methoxypropoxy, and lower alkoxy-lower alkoxy-lower alkoxy is especially ω-(ω-lower alkoxy-lower alkoxy)-lower alkoxy, for example 2-(2-methoxyethoxy)-ethoxy.

Di-lower alkylamino-lower alkyl is, for example, 2- and/or 3-di-lower alkylamino-lower alkyl, for example 2-dimethylaminoethyl, 2-diethylaminoethyl or 3-dimethylaminopropyl. Correspondingly, di-lower alkylamino-lower alkoxy and the same in di-lower alkylamino-lower alkoxycarbonyl are especially 2- and-/or 3-di-lower alkylamino-lower alkoxy, for example 2-dimethylaminoethoxy, 2-diethylaminoethoxy or 3-dimethylaminopropoxy.

Phenyl-lower alkyl is, for example, benzyl or 1- or 2-phenylethyl, and phenyl-lower alkoxy and the same in phenyl-lower alkoxycarbonyl are, for example, benzyloxy or 1- or 2-phenylethoxy.

Cycloalkyl is especially cycloalkyl having from 3 to 8, especially from 5 to 7, ring members, for example cyclopentyl, cyclohexyl or cycloheptyl, also cyclopropyl, cyclobutyl or cyclooctyl.

Furyl is, for example, 2-furyl, and, correspondingly, thienyl is, for example, 2-thienyl, while pyridyl may be 2-, 3- or 4-pyridyl.

Furyl-lower alkyl, thienyl-lower alkyl and pyridyl-lower alkyl have, as the alkyl moiety, especially methyl and are, for example, furfuryl, 2-thenyl or pyridylmethyl, such as 2- or 4-pyridylmethyl.

Mono- or di-lower alkylamino is, for example, methylamino, dimethylamino, ethylamino, diethylamino, propylamino or butylamino.

Lower alkyleneamino or aza-, oxa- or thia-lower alkyleneamino and the same in correspondingly substituted lower alkyl or lower alkoxy radicals are, for example, pyrrolidin-1-yl, piperidino, morpholino, thiamorpholino, or N-lower alkylpiperazin-1-yl, such as N'-methylpiperazin-1-yl.

Lower alkanoyloxy is, for example, acetoxy, propionyloxy, butyryloxy or pivaloyloxy.

Halogen is especially halogen having an atomic number of up to and including 35, such as fluorine, chlorine or bromine.

Salt-forming compounds of the formula (I) are, for example, acidic compounds containing carboxy $R_2$, $R_3$ or $R_1$—X—C(=O)— and/or enolic hydroxy groups, for example hydroxy $R_A$, or basic compounds of the formula (I) containing basic groups, optionally in addition to a smaller number of acidic groups. Salts of the same are, for example, salts of acidic compounds with bases, especially pharmaceutically acceptable salts, such as alkali metal or alkaline earth metal salts, for example sodium, potassium, magnesium or calcium salts, also ammonium salts with ammonia or amines, such as lower alkyl- or hydroxy-lower alkyl-amines, for example trimethylamine, triethylamine or di- or tri-(2-hydroxyethyl)-amine, or acid addition salts, especially pharmaceutically acceptable acid addition salts, for example salts with inorganic acids, such as mineral acids, for example hydrohalic acid, sulphuric acid or phosphoric acid, addition salts or acid addition salts with suitable organic sulphonic or carboxylic acids, for example hydrochlorides, hydrobromides, sulphates, phosphates, malates, maleates, fumarates or tartrates.

The invention relates, for example, to those compounds of the formula (I) in which X represents a direct bond and $R_1$, $R_2$, $R_3$, $R_4$, $R_5$, $R_A$, $R_B$, $R_C$, $R_D$, and $R_E$ have the meanings given at the beginning, $R_1$ being different from hydrogen, or in which X represents oxy, $R_1$ represents lower alkyl, or phenyl that is optionally substituted, for example as indicated, and $R_2$, $R_3$, $R_4$, $R_5$, $R_A$, $R_B$, $R_C$, $R_D$ and $R_E$ have the meanings given at the beginning, and their salts, processes for their manufacture, pharmaceutical preparations containing them and their use as the active ingredients of medicaments.

The invention relates especially to compounds of the formula (I) in which $R_1$ represents lower alkyl, lower alkenyl or cycloalkyl each of which is optionally substituted by hydroxy, lower alkoxy, hydroxy-lower alkoxy, lower alkoxy-lower alkoxy, hydrox-lower alkoxy-lower alkoxy, lower alkoxy-lower alkoxy-lower alkoxy, lower alkylthio, lower alkanesulphinyl or by lower alkanesulphonyl, phenyl or phenyl-lower alkyl each of which is optionally substituted in the phenyl moiety by lower alkyl, lower alkoxy and/or by halogen, furyl, thienyl or pyridyl, or furyl-lower alkyl, thienyl-lower alkyl or pyridyl-lower alkyl or hydrogen, Ph represents 1,2-phenylene that is optionally additionally substituted by lower alkyl, lower alkoxy, hydroxy and/or by halogen, $R_2$ represents carboxy, lower alkoxycarbonyl, hydroxy-lower alkoxycarbonyl, lower alkoxy-lower alkoxycarbonyl, di-lower alkylamino-lower alkoxy- or 5 to 7-membered lower alkyleneamino- or aza-, oxa- or thia-lower alkyleneamino-lower alkoxy-carbonyl or amidated carboxy containing, as amino group, amino, hydroxyamino, lower alkylamino, di-lower alkylamino or 5- to 7-membered lower alkylene- or aza-, oxa-, or thia-lower alkylene-amino, $R_3$ represents hydrogen, lower alkyl or hydroxy, and in which either $R_A$ and $R_B$ together represent oxo, $R_C$ and $R_D$ together represent an additional bond, or, when $R_2$ represents a radical $R_4$, $R_C$ is hydrogen and $R_3$ and $R_D$ together represent oxo, and $R_E$ represents hydrogen, lower alkyl, hydroxy-lower alkyl, lower alkoxy-lower alkyl, di-lower alkylamino-lower alkyl, 5- to 7-membered lower alkyleneamino- or aza-, oxa- or thia-lower alkyleneamino-lower alkyl, lower alkenyl, lower alkynyl, cycloalkyl having from 3 to 8, especially from 5 to 7, ring members, phenyl-lower alkyl, furyl-lower alkyl, thienyl-lower alkyl or pyridyl-lower alkyl, each of which is optionally substituted by lower alkyl, lower alkoxy and/or by halogen, or $R_A$ represents hydroxy or lower alkoxy, $R_B$ together with $R_C$ and also $R_D$ together with $R_E$ represent an additional bond in each case, or $R_B$ and $R_C$ together represent an additional bond and $R_3$ and $R_D$ together represent oxo, and $R_E$ represents hydrogen, lower alkyl, hydroxy-lower alkyl, lower alkoxy-lower alkyl, di-lower alkylamino-lower alkyl, 5- to 7-membered lower alkyleneamino- or aza-, oxa- or thia-lower alkyleneamino-lower alkyl, lower alkenyl, lower alkynyl, cycloalkyl having from 3 to 8, especially from 5 to 7, ring members, phenyl-lower alkyl, furyl-lower alkyl, thienyl-lower alkyl or pyridyl-lower alkyl, each of which is optionally substituted by lower alkyl, lower alkoxy and/or by halogen, and salts of the above-defined compounds having salt-forming properties.

The invention relates on the one hand especially to compounds of the formula (Ia)

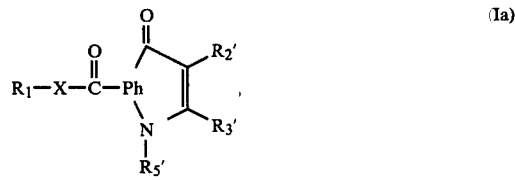

in which $R_1$ represents lower alkyl having up to 7 carbon atoms, for example propyl, isopropyl, butyl, isobutyl, tert-butyl, sec-butyl or pentyl; lower alkoxy-, lower alkylthio-, lower alkanesulphinyl- or lower alkanesulphonyl-lower alkyl each having up to 4 carbon atoms in the alkyl moiety, for example methanesulphinyl- or methanesulphonylmethyl; phenylthio-, benzenesulphinyl- or benzenesulphonyl-lower alkyl having up to 4 carbon atoms in the alkyl moiety, for example benzenesulphonylmethyl; lower alkenyl having up to 4 carbon atoms, for example allyl; 3- to 8-membered cycloalkyl, for example cyclopentyl, cyclohexyl or cycloheptyl; phenyl or phenyl-lower alkyl having up to 4 carbon atoms in the alkyl moiety, for example corresponding benzyl or 1- or 2-phenylethyl, each of which is optionally substituted by lower alkyl having up to 4 carbon atoms, for example methyl, lower alkoxy having up to 4 carbon atoms, for example methoxy, and/or by halogen having an atomic number of up to and including 35, for example chlorine or bromine; furyl, thienyl or pyridyl, for example 2-furyl, 2-thienyl or 2-, 3- or 4-pyridyl, or furyl-, thienyl- or pyridyl-lower alkyl having up to 4 carbon atoms in the alkyl moiety, for example furfuryl, 2-thenyl, or 2- or 4-picolyl, and X represents a direct bond or $R_1$ represents hydrogen or lower alkyl having up to 7 carbon atoms and X represents oxy, and in which Ph represents 1,2-phenylene that contains the group $R_1$—X—C($\equiv$O)— and that is optionally additionally substituted by lower alkyl having up to 4 carbon atoms, for example methyl, lower alkoxy having up to 4 carbon atoms, for example methoxy, hydroxy or by halogen having an atomic number of up to and including 35, for example chlorine, one of the radicals $R_2'$ and $R_3'$ represents carboxy, lower alkoxycarbonyl having up to 5 carbon atoms, for example methoxy- or ethoxy-carbonyl, hydroxy-lower alkoxycarbonyl having up to 5 carbon atoms, for example 2-hydroxyethoxycarbonyl, lower alkoxy-lower alkoxycarbonyl having up to 4 carbon atoms in the alkoxy moieties, for example 2-methoxy- or 2-ethoxy-ethoxycarbonyl, di-lower alkylamino-lower alkoxycarbonyl having up to 4 carbon atoms in the alkyl moiety and up to 4 carbon atoms in the alkoxy moiety, for example 2-dimethylaminoethoxy- or 2-diethylaminoethoxy-carbonyl, carbamoyl, N-hydroxycarbamoyl or N-lower alkyl- or N,N-di-lower alkyl-carbamoyl having up to 4 carbon atoms in the alkyl moiety, for example N-methyl-, N-ethyl- or N,N-dimethyl-carbamoyl, and the other represents hydrogen, lower alkyl having up to 4 carbon atoms, for example methyl, or, in the case of a radical $R_3'$, hydroxy, and $R_5'$ represents hydrogen; lower alkyl or lower alkenyl having up to 4 carbon atoms, for example methyl, ethyl or allyl; phenyl-, furyl-, thienyl- or pyridyl-lower alkyl that have up to 4 carbon atoms in the alkyl moiety and each of which is optionally substituted by lower alkyl having up to 4 carbon atoms, for example methyl, lower alkoxy having up to 4 carbon atoms, for example methoxy, and/or by halogen having an atomic number of up to and including 35, for example chlorine, for example corresponding benzyl, 1- or 2-phenylethyl, furfuryl, 2-thenyl or 2- or 4-picolyl; lower alkoxy-lower alkyl having up to 4 carbon atoms in the alkoxy moiety and up to 4 carbon atoms in the alkyl moiety, for example 2-methoxy- or 2-ethoxy-ethyl; or di-lower alkylamino-lower alkyl in which lower alkyl has up to 4 carbon atoms or lower alkylene or aza-, oxa- or thia-lower alkylene having from 5 to 7 ring members, for example 2-dimethylamino- or 2-diethylamino-ethyl, and tautomers thereof in which a hydroxy group $R_3$ is in the tautomeric oxo form, and salts of salt-forming compounds of the formula (Ia) or their tautomers.

The invention relates on the other hand especially to compounds of the formula

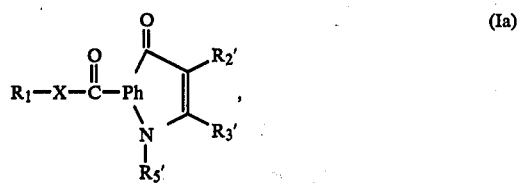

in which $R_1$ represents lower alkyl having up to 7 carbon atoms, for example propyl, isopropyl, butyl, isobutyl, tert-butyl, sec-butyl or pentyl, lower alkoxy-, lower alkylthio-, lower alkanesulphinyl- or lower alkanesulphonyl-lower alkyl each having up to 4 carbon atoms in the alkyl moiety, for example methanesulphinyl- or methanesulphonylmethyl, lower alkenyl having up to 4 carbon atoms, for example allyl, or 3- to 8-membered cycloalkyl, for example cyclopentyl, cyclohexyl or cycloheptyl, and X represents a direct bond, or $R_1$ represents hydrogen, lower alkyl having up to 7 carbon atoms, for example propyl, isopropyl, butyl, isobutyl, tert-butyl, sec-butyl or pentyl, lower alkoxy-, lower alkylthio-, lower alkanesulphinyl- or lower alkanesulphonyl-lower alkyl each having up to 4 carbon atoms in the alkyl moiety, for example methanesulphinyl- or methanesulphonyl-methyl, lower alkenyl having up to 4 carbon atoms, for example allyl, 3- to 8-membered cycloalkyl, for example cyclopentyl, cyclohexyl or cycloheptyl, ω-hydroxy-lower alkyl having from 2 to 4 carbon atoms, such as 2-hydroxyethyl, lower alkanoyloxymethyl having up to and including 7 carbon atoms in the alkanoyl moiety, such as acetoxy- or pivaloyloxy-methyl, or ω-(ω-hydroxy-lower alkoxy)-lower alkyl, ω-(ω-lower alkoxy-lower alkoxy)-lower alkyl, ω-[ω-(ω-hydroxy-lower alkoxy)-lower alkoxy]-lower alkyl or ω-[ω-(ω-lower alkoxy-lower alkoxy)-lower alkoxy]-lower alkyl each having from 1 to 4 carbon atoms in the alkyl moiety and from 2 to 4 carbon atoms in the alkylene moiety, such as 2-(2-hydroxyethoxy)-ethyl, 2-(2-methoxyethoxy)-ethyl, 2-[2-(2-hydroxyethoxy)-ethoxy]-ethyl or 2-[2-(2-methoxyethoxy)-ethoxy]-ethyl, and X represents oxy, and in which Ph represents 1,2-phenylene that contains the group $R_1$—X—CO— and is optionally additionally substituted by lower alkyl having up to 4 carbon atoms, for example methyl, lower alkoxy having up to 4 carbon atoms, for example methoxy, hydroxy or by halogen having an atomic number of up to and including 35, for example chlorine, $R_2'$ represents carboxy, lower alkoxycarbonyl having up to 5 carbon atoms, for example methoxy- or ethoxy-carbonyl, hydroxy-lower alkoxycarbonyl having up to 5 carbon atoms, for example 2-hydroxyethoxycarbonyl, lower alkoxy-lower alkoxycarbonyl having up to 4 carbon atoms in the alkoxy moieties, for example 2-methoxy- or 2-ethoxy-ethoxycarbonyl, carbamoyl, N-hydroxycarbamoyl or N-lower alkyl- or N,N-di-lower alkyl-carbamoyl having up to 4 carbon atoms in the alkyl moiety, for example N-methyl-, N-ethyl or N,N-dimethylcarbamoyl, $R_3'$ represents hydroxy, and $R_5'$ represents hydrogen, lower alkyl having up to and including 4 carbon atoms, for example ethyl, lower alkenyl having up to and including 4 carbon atoms, such as allyl, or lower alkynyl having up to and including 4 carbon atoms, such as propargyl, and tautomers thereof in which a hydroxy group $R_3'$ is in the tautomeric oxo form, and salts of salt-forming compounds of the formula (Ia) or their tautomers.

The invention relates more especially to compounds of the formula (II)

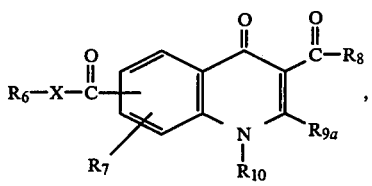

in which
X represents a direct bond and $R_6$ represents hydrogen or lower alkyl having up to 7 carbon atoms, for example propyl, isopropyl or especially butyl, also isobutyl, sec-butyl or pentyl, or X represents oxy and $R_6$ represents hydrogen, lower alkyl having up to 7 carbon atoms, for example propyl, isopropyl or especially butyl, also isobutyl, sec-butyl or pentyl, ω-hydroxy-lower alkyl having from 2 to 4 carbon atoms, such as 2-hydroxyethyl, lower alkanoyloxymethyl having up to and including 7 carbon atoms in the alkanoyl moiety, such as acetoxy- or pivaloyloxy-methyl, or ω-(ω-hydroxy-lower alkoxy)-lower alkyl, ω-(ω-lower alkoxy-lower alkoxy)-lower alkyl, ω-[ω-(ω-hydroxy-lower alkoxy)-lower alkoxy]-lower alkyl or ω-[ω-(ω-lower alkoxy-lower alkoxy)-lower alkoxy]-lower alkyl each having from 1 to 4 carbon atoms in the alkyl moiety and from 2 to 4 carbon atoms in the alkylene moiety, such as 2-(2-hydroxyethoxy)-ethyl, 2-(2-methoxyethoxy)-ethyl, 2-[2-(2-hydroxyethoxy)-ethoxy]-ethyl or 2-[2-(2-methoxyethoxy)-ethoxy]-ethyl, $R_7$ represents hydrogen or especially lower alkyl having up to and including 4 carbon atoms, for example methyl, or also lower alkoxy having up to and including 4 carbon atoms, for example methoxy, halogen having an atomic number of up to and including 35, for example chlorine, or hydroxy, $R_8$ represents hydroxy or lower alkoxy having up to 4 carbon atoms, for example methoxy or ethoxy, $R_{9a}$ represents hydrogen or especially hydroxy, and $R_{10}$ represents lower alkyl, lower alkenyl or lower alkynyl each having up to and including 4 carbon atoms, for example ethyl, allyl or propargyl, it also being possible for 2-hydroxy-4-oxo-1,4-dihydroquinoline compounds of the formula (II) to be in the tautomeric 2-oxo-4-hydroxy-1,2-dihydro- or 2,4-dioxo-1,2,3,4-tetrahydroquinoline form, and very especially to those in which the radical of the formula $R_6$—X—C(=O)— is in the 6-position and a radical $R_7$ that is not hydrogen is in the 5- or 7-position of the quinoline ring system, and salts of salt-forming compounds of the formula (II) or of their tautomers.

Of particular importance in accordance with the invention are compounds of the formula (II) in which X represents oxy, the group $R_6$—O—C(=O)— is bonded in the 6-position, $R_6$ is hydrogen, lower alkyl having up to 7 carbon atoms, for example butyl, isobutyl, or sec-butyl, lower alkanoyloxymethyl having up to and including 7 carbon atoms in the alkanoyl moiety, such as acetoxy- or pivaloyloxy-methyl, or ω-(ω-hydroxy-lower alkoxy)-lower alkyl, ω-(ω-lower alkoxy-lower alkoxy)-lower alkyl, ω-[ω-(ω-hydroxy-lower alkoxy)-lower alkoxy]-lower alkyl or ω-[ω-(ω-lower alkoxy-lower alkoxy)-lower alkoxy]-lower alkyl each having from 1 to 4 carbon atoms in the alkyl moiety and from 2 to 4 carbon atoms in the alkylene moiety, such as 2-(2-hydroxyethoxy)-ethyl, 2-(2-methoxyethoxy)-ethyl, 2-[2-(2-hydroxyethoxy)-ethoxy]-ethyl or 2-[2-(2-methoxyethoxy)-ethoxy]-ethyl, $R_7$ represents hydrogen, $R_8$ represents hydroxy or lower alkoxy having up to and including 4 carbon atoms, for example methoxy or ethoxy, $R_{9a}$ represents hydroxy, and $R_{10}$ represents lower alkenyl having up to and including 4 carbon atoms, for example allyl, or X represents a direct bond, $R_6$ represents hydrogen or lower alkyl having up to and including 7 carbon atoms, such as propyl, $R_7$ represents lower alkyl having up to and including 4 carbon atoms, such as methyl, the group $R_6$—C(=O)— taking up the 6-position and the lower alkyl group $R_7$ the 7-position, $R_8$ represents hydroxy or lower alkoxy having up to and including 4 carbon atoms, such as methoxy or ethoxy, $R_{9a}$ represents hydroxy and $R_{10}$ represents lower alkyl having up to and including 4 carbon atoms, such as propyl, or the 2-oxo-4-hydroxy-1,2-dihydroquinoline or 2,4-dioxo-1,2,3,4-tetrahydroquinoline tautomer thereof in free form or in salt form.

The invention relates most especially to compounds of the formula (II) in which X represents a direct bond and $R_6$ represents lower alkyl having up to 7 carbon atoms, for example propyl, or X represents oxy and $R_6$ represents hydrogen or lower alkyl having up to and including 4 carbon atoms, such as methyl, and in which $R_7$ represents hydrogen or especially lower alkyl having up to and including 4 carbon atoms, such as methyl, the group $R_6$—X—C(=O)— preferably taking up the 6-position and lower alkyl $R_7$ preferably the 7-position, $R_8$ represents hydroxy or lower alkoxy having up to 4 carbon atoms, such as ethoxy, $R_{9a}$ represents hydroxy and $R_{10}$ represents lower alkyl or lower alkenyl having up to 4 carbon atoms, such as methyl, ethyl, propyl or allyl, and their 2-oxo-4-hydroxy-1,2-dihydroquinoline or 2,4-dioxo-1,2,3,4-tetrahydroquinoline tautomers, and, if appropriate, salts, especially pharmaceutically acceptable salts, of salt-forming compounds of the type mentioned.

The invention relates especially to the specific compounds of the formula (I) mentioned in the Examples.

The compounds of the formula (I) can be manufactured according to methods known per se, for example by subjecting a compound of the formula (IV)

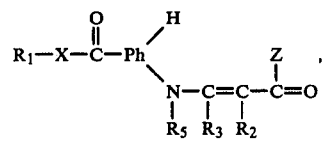

in which Z is a removable radical, or a tautomer and/or salt thereof, to intramolecular cyclisation and, if desired, converting the resulting compound into a different compound of the formula (I) and/or converting a resulting free compound into a salt or a resulting salt into the free compound or into a different salt.

The removable radical Z is, for example, an optionally etherified or esterified hydroxy group. Etherified hydroxy groups are, for example, hydroxy groups etherified by aliphatic, araliphatic or aromatic alcohols, such as lower alkoxy, for example methoxy or ethoxy, or optionally substituted phenoxy, such as phenoxy containing lower alkyl, lower alkoxy or especially halogen and/or nitro, for example phenoxy, 4-chlorophenoxy, 4-nitrophenoxy, 2,4-dinitrophenoxy and 3,5-dichlorophenoxy. Esterified hydroxy groups are, for example, hydroxy groups esterified by organic carboxylic acids, such as lower alkanoic acids, or by monofunctional carbonic acid derivatives, such as carbonic acid monoesters or monohalides, but especially by mineral acids, such as hydrohalic acids, for example formyloxy, acetoxy, chlorocarbonyloxy, lower alkoxycarbonyloxy, such as ethoxycarbonyloxy, or especially halogen atoms, such as chlorine, bromine or iodine, also sulphonyloxy groups, such as sulphonyloxy groups derived from organic sulphonic acid or halosulphonic acids, for example fluorosulphonyloxy, chlorosulphonyloxy, methanesulphonyloxy, benzenesulphonyloxy, p-toluenesulphonyloxy or p-bromosulphonyloxy. Tautomers of compounds of the formula (IV) are especially those in which a hydroxy group $R_3$ is in the tautomeric oxo form. Salts of compounds of the formula (IV) are especially salts with bases, such as alkali metal salts, of compounds of the formula (IV) in which Z is hydroxy and/or $R_4$ is carboxy, or acid addition salts of basic compounds of the formula (IV).

The intramolecular condensation can be carried out in customary manner, preferably by heating, for example to from approximately 150° C. to approximately 250° C., in the presence of a suitable condensation agent and, if necessary, of a solvent that is inert under the reaction conditions, and, if necessary, under an inert gas, such as nitrogen, and/or in a closed vessel. Solvents that are inert under the reaction conditions are, for example, higher-boiling hydrocarbons, such as toluene or xylene, ethers, such as diphenyl ether, or tertiary carboxylic acid amides, such as dimethylformamide or N-methylpyrrolidone. Suitable condensation agents are, for example, acidic agents, such as protonic acids, for example mineral acids, inter alia sulphuric acid, phosphoric acid or polyphosphoric acid, or acidic mineral acid esters, such as mono- or di-lower alkyl phosphates or phosphites, inter alia triethyl phosphate, triethyl phosphite or tetraethyl pyrophosphate, also Lewis acids, such as, for example, aluminium chloride, aluminium bromide, zinc chloride, boron trifluoride or antimony pentachloride.

The starting materials of the formula (IV), insofar as they are novel, can be obtained according to methods known per se, for example starting from corresponding aniline compounds of the formula $R_1$—X—C(=O)—Ph(NHR$_5$)—H (V). Thus, starting materials of the formula (IV) in which $R_2$ represents a radical $R_4$ and Z represents an etherified hydroxy group, can be obtained, for example, by condensing the above-mentioned aniline compound in customary manner with a lower alkoxy-$R_3$-methylenemalonic acid ester. From the resulting esters of the formula (IV) there can be manufactured in customary manner, for example by hydrolysis, the corresponding acids, and from those, in customary manner, other functional derivatives of the same. Starting materials of the formula (IV) in which $R_3$ represents a radical $R_4$ and Z represents optionally etherified hydroxy, are obtained, for example, by condensing the above-mentioned aniline compound with a suitable aliphatic 1,4-dicarboxylic acid derivative, for example with chlorofumaric acid, acetylenedicarboxylic acid or oxalacetic acid, or a suitable functional carboxy derivative thereof, such as a diester, ester halide or dihalide thereof, and, if desired, hydrolysing a resulting functional carboxy derivative to the acid and/or converting a resulting acid into a different functional derivative. Thus, the reaction can be carried out, for example in the manner of a Conrad-Limpach reaction, in an aromatic or aliphatic hydrocarbon, for example in benzene or toluene, with an oxalacetic acid mono-lower alkyl ester or an oxalacetic acid di-lower alkyl ester, the operation being carried out preferably at elevated temperature, for example at from 50° to 150° C., especially at from 80° to 110° C., and advantageously with the azeotropic-distillative removal of the reaction water. Alternatively, the reaction can be carried out in known manner, for example in the presence of a basic condensation agent, such as sodium or potassium hydroxide, pyridine or triethylamine, with an oxalacetic acid ester chloride or chlorooxalylacetic acid or, preferably in an alkanol, such as methanol, with an acetylenedicarboxylic acid di-lower alkyl ester, for example with acetylenedicarboxylic acid dimethyl ester.

Compounds of the formula (I) in which $R_2$ represents a radical $R_4$ and $R_3$ represents hydroxy, or tautomers of the same, can also be manufactured by subjecting a compound of the formula (VI)

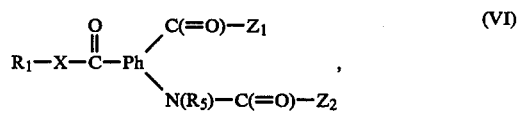

in which one of the radicals $Z_1$ and $Z_2$ represents a group of the formula $CH_2$—$R_4$ and the other represents an optionally reactively etherified or esterified hydroxy group, or a tautomer and/or salt thereof, to intramolecular cyclisation, and, if desired, converting the resulting compound into a different compound of the formula (I) and/or converting a resulting free compound into a salt or a resulting salt into the free compound or into a different salt.

Etherified hydroxy groups are, for example, hydroxy groups etherified by an aliphatic alcohol, such as by a lower alkanol, for example by methanol or ethanol, or by an optionally substituted aromatic alcohol, for example phenol. Esterified hydroxy groups are, for example, hydroxy groups esterified by a mineral acid, such as a hydrohalic acid, for example by hydrochloric, hydrobromic or hydriodic acid, or, less favourably, by a halosulphonic acid or an organic sulphonic acid, for example methane-, ethane-, benzene-, p-toluene-, or fluorosulphonic acid.

The intramolecular cyclisation is carried out in customary manner, preferably in a substantially anhydrous solvent, advantageously in the presence of a dehydrating agent and, if necessary, in the presence of a basic condensation agent, if necessary at elevated temperature, for example at approximately from 50° to 150° C., under an inert gas, such as nitrogen, and/or in a closed vessel. Suitable solvents are especially lower alkanols, such as methanol, ethanol or butanol, lower alkylene glycols, such as ethylene glycol, also dimethyl sulphoxide, dimethylformamide, diphenyl ether and high-boiling hydrocarbons, such as xylene. Basic condensation agents are, for example, alkali alcoholates, such as alkali-lower alkoxides, for example sodium methoxide, sodium ethoxide or sodium tert-butoxide, or alkali metal hydrides, such as sodium hydride.

The starting materials of the formula (VI), insofar as they are novel, can be manufactured according to methods known per se, for example by reacting a compound of the formula $R_1$—X—C(=O)—Ph(NHR$_5$)—C(=O)—$Z_1$ (VIII), or a derivative thereof, with a compound of the formula $Z_2$—COOH (VIII), or with a reactive functional derivative thereof, such as an ester, for example a lower alkyl ester, or an anhydride, for example the chloride, or the symmetric or internal anhydride, thereof, and, if desired, in the resulting compound of the formula (VI), converting groups $Z_1$ and/or $Z_2$ in customary manner into other such groups. Thus, for example, a corresponding anthranilic acid ester can be reacted with a malonic acid ester chloride or a malonic acid diester, or a corresponding 2-aminobenzoylacetic acid ester can be reacted with phosgene or a haloformic acid lower alkyl ester or a haloformic acid phenyl ester.

Compounds of the formula (I) in which $R_2$ represents a radical $R_4$ and $R_3$ represents hydroxy can also be manufactured by subjecting a compound of the formula (IX)

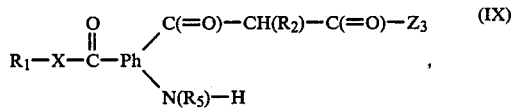

in which $Z_3$ represents hydroxy or a reactive modified hydroxy group, or a tautomer and/or salt thereof, to intramolecular condensation and, if desired, converting a resulting compound into a different compound of the formula (I) and/or converting a resulting free compound into a salt or a resulting salt into the free compound or into a different salt.

Reactive modified hydroxy groups are, for example, etherified or especially esterified hydroxy groups. Etherified hydroxy groups are, for example, lower alkoxy or optionally substituted phenoxy, and esterified hydroxy groups are hydroxy groups esterified especially by mineral acids, such as hydrohalic acids, or by halosulphonic acids or organic sulphonic acids, such as halogen, for example chlorine, bromine or iodine, or methane-, benzene-, p-toluene, p-bromobenzene- or fluoro-sulphonyloxy. The intramolecular cyclisation of compounds of the formula (IX) can be carried out in customary manner, for example in a solvent that is inert under the reaction conditions, such as a hydrocarbon, for example benzene, toluene or mineral oil, an ether, for example diethyl ether or tetrahydrofuran, dimethylformamide, dimethyl sulphoxide, and the like, if necessary while heating, for example to approximately from 50° to 150° C., advantageously in the presence of a basic condensation agent, such as an alkali metal hydroxide, for example sodium or potassium hydroxide, or an organic nitrogen base, such as pyridine or triethylamine, if necessary under an inert gas, such as nitrogen, and/or in a closed vessel.

The starting materials of the formula (IX), insofar as they are novel, can be manufactured according to methods known per se, for example by reacting in customary manner a compound of the formula $R_1$—X—C(=O)—Ph—(NHR$_5$)—COOH (X) or a functional carboxy derivative, such as an ester or an anhydride, for example the symmetric anhydride, a corresponding acid chloride or the corresponding isatic acid anhydride, with malonic acid or a suitable functional derivative, such as a diester, of the same, and, if desired, in the resulting compound, converting the group $Z_3$ into a different such group.

The compounds of the formula (I) can also be manufactured by, in a compound of the formula (XI)

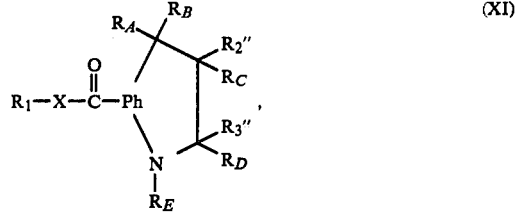

in which one of the radicals $R_2''$ and $R_3''$ represents a radical $R_4'$ that can be converted into the optionally esterified or amidated carboxy group $R_4'$ and the other represents hydrogen or an aliphatic radical or, in the case of a radical $R_3''$, hydroxy, or in a tautomer and/or salt thereof, converting the group $R_4'$ into the optionally esterified or amidated carboxy group $R_4$ and, if desired, converting a resulting compound into a different compound of the formula (I) or converting a resulting salt-forming compound into a salt or a resulting salt into the free compound or into a different salt.

Groups $R_4'$ which can be converted into optionally esterified or amidated carboxy are, for example, functionally modified carboxy groups that can be converted by solvolysis into optionally esterified or amidated carboxy and that are other than esterified or amidated carboxy $R_4$. Such groups are, for example, cyano, anhydridised carboxy groups, iminoether groups, iminoester groups and etherified and/or esterified trihydroxymethyl groups. Anhydridised carboxy groups are, for example, carboxy groups anhydridised by a mineral acid, such as a hydrohalic acid, by a halosulphonic acid, such as fluorosulphonic acid, or an organic sulphonic or carboxylic acid, such as an aliphatic or aromatic sulphonic or carboxylic acid. Iminoether groups are, for example, iminoether groups derived from esterified carboxy groups $R_4$, such as O-lower alkylcarbamoyl, or cyclic iminoether groups, such as 4,4- or 5,5-di-lower alkyl-, for example 4,4- or 5,5-dimethyl-4,5-dihydrooxazol-2-yl, or 4,4,6-tri-lower alkyl-, for example 4,4,6-trimethyl-, 5,6-dihydrooxazin-2-yl. Iminoester groups are, for example, iminoester groups that are derived from amidated carboxy groups $R_4$ and that are esterified by hydrohalic acids or organic carboxylic acids, such as lower alkanoic acids, such as, for example, chlorocarbimino or O-lower alkanoylcarbamoyl. Etherified and/or esterified trihydroxymethyl groups are, for example, trihydroxymethyl groups that are esterified by mineral acids, such as hydrohalic acids, and/or etherified and that correspond to esterified carboxy groups $R_4$, for example tri-lower alkoxymethyl, lower alkoxy dihalomethyl or trihalomethyl, especially those in which halogen is chlorine or bromine. Further groups that can be converted by solvolysis into amidated carboxy groups $R_4$ are, for example, dihalogenated carbamoyl groups corresponding to those groups, i.e. corresponding aminodihalo-, especially -dichloro-methyl groups.

The mentioned groups can be converted by customary hydrolysis into carboxy groups; iminoether groups and etherified hydroxydihalomethyl groups, such as lower alkoxydihalomethyl groups, can similarly be converted into esterified carboxy groups, aminodihalomethyl groups into amidated carboxy groups and cyano into unsubstituted carbamoyl groups. The hydrolysis is carried out in customary manner, for example in the presence of an acidic or alkaline hydrolysis agent, generally in the presence of a solvent and/or diluent or a mixture thereof, and, if necessary, while cooling or heating, for example in a temperature range of from approximately 0° C. to approximately 120° C., if necessary under an inert gas, such as nitrogen, and/or in a closed vessel. Acidic hydrolysis agents are, for example, mineral acids, such as hydrohalic acids, for example hydrochloric acid, or oxygen acids of sulphur or phosphorus, such as sulphuric or phosphoric acid, also organic sulphonic acids, for example p-toluenesulphonic acid or mesitylenesulphonic acid, or organic carboxylic acids, such as lower alkanecarboxylic acids, for example formic or acetic acid. Basic hydrolysis agents are, for example, alkali metal hydroxides, for example sodium or potassium hydroxide, also alkali metal carbonates, for example sodium or potassium carbonate. Suitable solvents or diluents are preferably water-miscible solvents, such as lower alkanols, for example ethanol or methanol, lower ketones, for example acetone, or tertiary alkanoic acid amides, for example dimethylformamide or N-methylpyrrolidone.

Anhydridised carboxy groups and cyclic iminoether groups can also be converted by alcoholysis, i.e. reaction with a corresponding alcohol, into esterified carboxy groups $R_4$. This operation is carried out in customary manner, starting from anhydridised carboxy groups, for example in the presence of a basic condensation agent, such as an alkali metal hydroxide or carbonate, for example sodium or potassium hydroxide or corresponding carbonates, or in the presence of organic nitrogen bases, such as pyridine or triethylamine, and, starting from cyclic iminoether groups, preferably under anhydrous conditions, for example in the presence of hydrogen chloride, phosphoric acid, sulphuric or p-toluenesulphonic acid, if necessary while heating, for example in a temperature range of from approximately 0° C. to approximately 150° C., under an inert gas, such as nitrogen, and/or in a closed vessel.

Anhydridised carboxy groups can also be converted in customary manner into amidated carboxy groups $R_4$ by ammonolysis or aminolysis, i.e. reaction with, respectively, ammonia or a corresponding amine having at least one hydrogen atom.

Further radicals $R_4'$ that can be converted into optionally esterified carboxy groups $R_4$ are groups that can be converted by oxidation into those groups, such as the optionally hydrated formyl group that can be converted by oxidation into carboxy, or etherified hydroxymethyl groups that can be converted by oxidation into esterified carboxy groups. Further groups that can be converted by oxidation into carboxy are optionally substituted 2-furyl containing, for example, di-lower alkoxymethyl, such as diethoxymethyl, in the 5-position, or optionally 2-substituted vinyl, for example 2,2-diphenylvinyl.

The oxidation can be carried out in a manner known per se, for example by reaction with an oxidising heavy metal compound, preferably a compound containing chromium(VI) or manganese(VII), for example with chromium trioxide or especially potassium permanganate, also with compounds containing bismuth(III), manganese(IV) or silver(I), for example with bismuth oxide, manganese dioxide or silver oxide, or by air oxidation. The operation is advantageously carried out in the presence of a solvent that is inert towards the reactants, for example acetone or pyridine, or a, preferably aqueous, mixture thereof, if necessary while cooling or heating, for example in a temperature range of approximately from 0° C. to 80° C. Optionally etherified hydroxymethyl can advantageously be oxidised by potassium permanganate in aqueous acetone or pyridine to optionally esterified carboxy.

The starting materials of the formula (XI), insofar as they are novel, can be manufactured according to methods known per se.

Compounds of the formula (XI) in which $R_4'$ represents cyano, etherified hydroxymethyl, formyl or optionally substituted 2-furyl, can be manufactured, for example, by intramolecular condensation of corresponding compounds of the formula $R_1$—X—C(=O)—Ph(H)—N($R_5$)—C($R_3''$)=C($R_2''$)—C(=O)—Z (XII) in which Z represents a reactively esterified or etherified hydroxy group, for example halogen or lower alkoxy, such as methoxy. A formyl group $R_4'$ may also be in intermediately protected, such as acetalised or acylalised, form, for example it may be in the form of di-lower alkoxy-, lower alkylenedioxy- or dihalomethyl. The nitriles of the formula (XI), obtainable, for example, in this manner, can be converted by customary reaction, for example acid-catalysed reaction, with the corresponding alcohols or amino alcohols, into iminoethers of the formula (XI), for example with a lower alkanol into open-chain iminoethers or with the appropriate aminoalkanol or alkanediol, for example with 4-amino-2-methylpentan-2-ol or 2-methylpentan-2,4-diol, into cyclic iminoethers. Compounds of the formula (XI) having a trihalomethyl group $R_4'$ can be obtained, for example, by customary halogenation of a corresponding methyl compound, for example with N-chloro- or N-bromosuccinimide, or by analogous haloform degradation of corresponding alkanoyl, such as acetyl, compounds. Compounds of the formula (XI) having an optionally hydrated formyl group $R_4'$ can also be formed in situ in the course of the oxidation reaction, for example from the methyl or aminomethyl group, or from the hydroxymethyl group optionally esterified by an inorganic acid, such as a hydrohalic acid or by an organic carboxylic acid, such as a lower alkanecarboxylic acid, or it can be freed from one of its derivatives, such as an acetal, acylal or imine, for example a lower alkylene- or di-lower alkyl-acetal of a dihalomethyl compound, such as a dichloromethyl compound, or an optionally substituted benzylimine. Amino- or lower alkoxy dihalo-methyl groups are likewise advantageously manufactured in situ by customary partial ammonolysis or aminolysis or alcoholysis of the corresponding trihalomethyl compound.

The compounds of the formula (I) can also be manufactured by, in a compound of the formula (XIII)

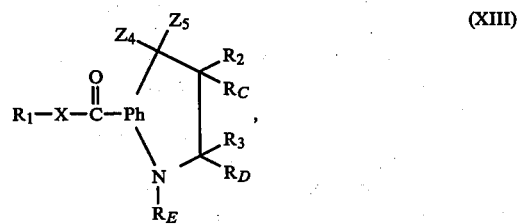

(XIII)

in which $Z_4$ represents a radical that can be converted into optionally etherified hydroxy, and $Z_5$ together with $R_C$ and $R_D$ together with $R_E$ represent an additional bond in each case, or in which $Z_4$ and $Z_5$ each represents a monovalent, or together represent a divalent, radical that can be converted into oxo and $R_C$ together with $R_D$ represents an additional bond, or in a salt thereof, converting into optionally etherified hydroxy a radical $Z_4$ that can be converted into optionally etherified hydroxy, or converting together into oxo radicals $Z_4$ and $Z_5$ that can be converted into oxo, and, if desired, converting the resulting compound into a different compound of the formula (I) and/or converting a resulting salt-forming compound into a salt or a resulting salt into the free compound or into a different salt.

Radicals that can be converted into optionally etherified hydroxy are, for example, esterified hydroxy groups, optionally etherified mercapto groups, sulphinyl groups, sulphonyl groups or optionally substituted amino groups. Monovalent radicals that can be converted jointly into the oxo group are, for example, esterified hydroxy groups or hydroxy groups etherified by a monohydric open-chain alcohol or mercapto groups etherified by an open-chain mercaptan. Divalent radicals that can be converted into oxo and that are represented by $Z_4$ and $Z_5$ together are, for example, the thio group or hydroxy groups etherified by a dihydric alcohol, mercapto alcohol or by mercaptan, or optionally substituted imino groups. Esterified hydroxy groups are, for example, hydroxy groups esterified by a mineral acid, an organic sulphonic acid or a carboxylic acid, such as halogen, for example chlorine, bromine or iodine, aliphatic or aromatic sulphonyloxy, for example methane-, ethane-, benzene- or p-toluenesulphonyloxy, or acyloxy derived from an organic carboxylic acid or a monofunctional carbonic acid derivative, such as a carbonic acid semiester, a haloformic acid or from optionally substituted carbamic acid, for example lower alkanoyloxy, optionally substituted benzoyloxy, lower alkoxycarbonyloxy, optionally substituted phenoxycarbonyloxy, chloro- or bromo-carbonyloxy or optionally substituted, such as lower alkylated, carbamoyloxy. Etherified mercapto is, for example, an aliphatic- or arylthio group, for example lower alkylthio or optionally substituted phenylthio. Substituted amino is, for example, amino mono-substituted by hydroxy or amino or mono- or di-substituted by aliphatic radicals or optionally substituted phenyl, it being possible for aliphatic radicals to be mono- or di-valent, monovalent aliphatic radicals being, for example, lower alkyl and divalent aliphatic radicals being, for example, lower alkylene or aza-, oxa- or thia-lower alkylene, for example hydroxyamino, hydrazino, mono- or di-lower alkylamino, optionally substituted anilino, pyrrolidin-1-yl, piperidino, morpholino, thiamorpholino or N'-lower alkylpiperazin-1-yl, such as N'-methylpiperazin-1-yl. Hydroxy etherified by a monohydric alcohol is, for example, lower alkoxy or optionally substituted phenyloxy. Hydroxy groups $Z_4+Z_5$ etherified by a dihydric alcohol are, for example, lower alkylenedioxy or optionally substituted 1,2-phenylenedioxy groups, for example ethylenedioxy, 1,3-propylenedioxy or 1,2-phenylenedioxy. Hydroxy groups etherified by a dihydric mercapto alcohol or mercaptan are, for example, lower alkylenedithio or lower alkyleneoxythio groups or optionally substituted 1,2-phenyldithio groups or phenoxythio groups, for example ethylenedithio, 1,3-propylenedithio or 1,2-phenylenedithio. Optionally substituted imino groups are, for example, imino groups substituted by hydroxy, amino, lower alkyl or optionally substituted phenyl, for example oximino, hydrazono, lower alkylimino or anilo.

The conversion of the mentioned groups into optionally etherified hydroxy or into oxo is carried out in customary manner, preferably by solvolysis, especially hydrolysis or alcoholysis, i.e. reaction with water or the alcohol corresponding to the etherified hydroxy group to be formed. Thus, for example, the mentioned groups that can be converted into oxo or into hydroxy can be converted into oxo or hydroxy in customary manner, for example in the presence of an acidic or basic hydrolysis agent, advantageously in a solvent or diluent and, if necessary, at elevated or reduced temperature, for example in the temperature range of from 0° to 150° C., under an inert gas, such as nitrogen, and/or in a closed vessel. Acidic hydrolysis agents are, for example, protonic acids, such as mineral acids or their acidic salts, for example hydrochloric, hydrobromic or hydriodic acid, sulphuric acid or alkali metal bisulphates, sulphonic acids, for example p-toluenesulphonic acid or sulphamic acid or organic carboxylic acids, such as lower alkanoic acids, also acidic ion exchangers. Basic condensation agents are, for example, alkali metal hydroxides or carbonates, for example sodium or potassium hydroxide or carbonate, also tertiary organic nitrogen bases, for example triethylamine or pyridine. Suitable solvents or diluents are especially water-miscible solvents, such as alcohols, for example lower alkanols, cyclic aliphatic ethers, for example dioxan or tetrahydrofuran, lower aliphatic ketones, for example acetone, tertiary aliphatic amides or lactams, for example dimethylformamide or N-methylpyrrolidone, or aliphatic sulphoxides, for example dimethyl sulphoxide. As already mentioned, reactively esterified hydroxy groups $Z_4$, i.e. hydroxy groups $Z_4$ esterified by a mineral acid or an organic sulphonic acid, can be converted according to customary methods of alcoholysis into etherified hydroxy, for example in the presence of a basic condensation agent, such as an alkali metal hydroxide or carbonate, or by using the appropriate alcohol in the form of an alcoholate, such as the appropriate alkali metal alcoholate, preferably in a solvent or diluent, if necessary while heating, for example in the temperature range of approximately from 0° to 150° C., and under an inert gas, such as nitrogen, and/or in a closed vessel.

The starting materials of the formula XIII, insofar as they are novel, can be manufactured according to methods known per se.

Thus, compounds of the formula XIII in which $Z_4$ represents halogen can be obtained, for example, by condensing a compound of the formula XIV

in the presence of a Lewis acid, for example aluminium trichloride, with a halide of the acid of the formula $R_1$—COOH (XV). There can be obtained from the resulting halogen compounds by reaction with an isothiuronium salt and subsequent hydrolysis, or by reaction with sodium thiolacetate and subsequent reduction, compounds of the formula (XIII) in which $Z_4$ is mercapto, or, by reaction with an alkali metal mercaptide, compounds of the formula (XIII) in which $Z_4$ is etherified mercapto. Compounds of the formula (XIII) in which $Z_4$ represents an optionally substituted amino group and $R_2$ represents an optionally esterified or amidated carboxy group can be manufactured, for example, by condensing a compound of the formula R₁—X—C(-
=O)—Ph(NHR₅)—C(Z₄)=CHR₂ (XVI) with a compound of the formula R₃—COOH (XVII) or preferably with an anhydride, such as the chloride, thereof. Compounds of the formula (XIII) in which Z₄ and Z₅ represent etherified hydroxy or mercapto can be manufactured, for example, by reacting a compound of the formula (XVIII)

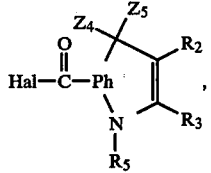

(XVIII)

in which Hal represents halogen, with a metal compound derived from the hydrocarbon of the formula R₁H, for example a corresponding halomagnesium or lithium compound. Compounds of the formula (XIII) in which Z₄+Z₅ represents imino can be obtained, for example, by condensing a compound of the formula R₁—X—C(=O)—Ph(NHR₅)—H (V) with an R₃ methylenecyanoacetic acid or an R₃ methylenemalodinitrile or R₃ methylenemalonic acid ester nitrile, the condensation being carried out preferably in the manner indicated for the manufacture and intramolecular condensation of compounds of the formula IV and VI.

The compounds of the formula I can also be obtained by, in a compound of the formula (XIX)

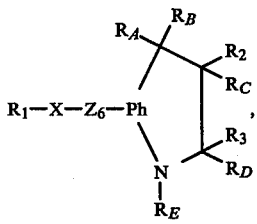

(XIX)

in which Z₆ represents a radical that can be converted into the carbonyl group, or in a salt thereof, converting Z₆ into the carbonyl group and, if desired, converting the resulting compound into a different compound of the formula I and/or converting a resulting salt-forming compound into a salt or a resulting salt into the free compound or into a different salt.

The radical Z₆ which can be converted into the carbonyl group is, for example, a radical that can be converted by solvolysis, especially hydrolysis, into that group, such as a functionally modified carbonyl group, for example thioxomethylene, optionally substituted iminomethylene or etherified or esterified dihydroxymethylene. Substituted iminomethylene groups are, for example, methyleneimino groups substituted by hydroxy, amino, lower alkyl or optionally substituted phenyl. Etherified dihydroxymethylene groups are, for example, dihydroxymethylene groups etherified by aliphatic alcohols, such as lower alkanols or lower alkanediols. Esterified dihydroxymethylene groups are, for example, dihydroxymethylene groups esterified by a hydrohalic acid, such as dichloro- or dibromo-methylene.

The conversion of the mentioned groups Z₆ into carbonyl is carried out according to customary methods of solvolysis, especially hydrolysis, for example in the presence of an acidic or basic hydrolysis agent, advantageously in a suitable solvent or diluent, if necessary while cooling or heating, for example in the temperature range of from approximately 0° to approximately 150° C., under an inert gas, such as nitrogen, and/or in a closed vessel. Acidic hydrolysis agents are, for example, protonic acids, such as mineral acids, for example hydrochloric, hydrobromic or hydriodic acid, sulphuric acid or phosphoric acid, or the acidic salts thereof, for example potassium bisulphate, sulphonic acids, such as aliphatic or aromatic sulphonic acids, for example methane-, ethane- or p-toluene-sulphonic acid, sulphamic acid, or organic carboxylic acids, such as lower alkanecarboxylic acids. Suitable solvents or diluents are, for example, water-miscible solvents, such as aliphatic alcohols, for example lower alkanols or lower alkanediols, cyclic aliphatic ethers, for example dioxan or tetrahydrofuran, di-lower alkyl ketones, for example acetone, or tertiary lower alkanecarboxylic acid amides or lactams, for example dimethylformamide or N-methylpyrrolidone.

Further radicals that can be converted into carbonyl groups are groups that can be oxidised to form those groups, for example the hydroxymethylene group, which can also be formed in situ under the reaction conditions, for example by oxidation of the methylene group, or it can be freed from one of its functional derivatives, for example an ester, such as a mineral acid or carboxylic acid ester, for example from a halomethylene group, a lower alkanoyloxymethylene group or an optionally substituted benzoyloxymethylene group.

The oxidation can be carried out in a manner known per se, for example by treatment with oxidising heavy metal compounds, such as compounds containing chromium(VI), manganese(VII) or (IV), silver or bismuth, for example with chromic acid, potassium dichromate, potassium permanganate, manganese dioxide, silver oxide or silver acetate or bismuth oxide, with oxidising inorganic oxy-acids or their salts, for example with sodium hypochlorite, sodium hypoiodite, sodium chlorate, sodium iodate or sodium metaperiodate, or with organic oxidising agents, such as quinones, for example benzoquinone or 2,6-dicyanobenzoquinone, dimethyl sulphoxide/N-chlorosuccinimide or dimethyl sulphide-ditrifluorosulphonate advantageously in a solvent or diluent that is inert towards the reactants, if necessary while cooling or heating, for example in the temperature range of approximately from −20° to 100° C., under an inert gas, such as nitrogen, and/or in a closed vessel. Especially advantageous is the use of potassium permanganate or manganese dioxide in aqueous acetone or aqueous pyridine, as the case may be, or of chromium trioxide in hexamethylphosphoric acid triamide.

The starting materials of the formula XIX, in so far as they are novel, can be manufactured, for example, by condensing a compound of the formula R₁—X—C(-=O)—Ph(NHR₅)—H (V) in customary manner, for example as described for the manufacture and intramolecular cyclisation of compounds of the formula IV, with a compound of the formula HO—C(R₃)(R_D)—C(R₂)(R_C)—COOH (XX) or a functional derivative, such as an ester and/or an ether, thereof in customary manner, for example as indicated for the manufacture and intramolecular condensation of compounds of the formula IV. Compounds of the formula XIX in which Z₆ represents hydroxymethylene, iminomethylene or etherified dihydroxymethylene, can also be obtained by reacting a corresponding aldehyde, nitrile or orthocarboxylic acid ester with a metal compound of the appropriate hydrocarbon of the formula $R_1H$, for example with a corresponding halomagnesium or lithium compound. Compounds of the formula XIX in which $Z_6$ represents dihalomethylene can also be manufactured by introducing the $R_1$ dihalomethyl radical into a corresponding compound that is unsubstituted in the benzene ring, for example by reaction with the corresponding $R_1$ trihalomethane in the presence of aluminium chloride.

Compounds of the formula I in which $R_A+R_B$ represents oxo, $R_C+R_D$ represents an additional bond, $R_2$ represents optionally esterified or amidated carboxy $R_4$, and $R_3$ represents optionally etherified hydroxy and $R_E$ represents a radical $R_5$, can also be manufactured by, in a compound of the formula XXI

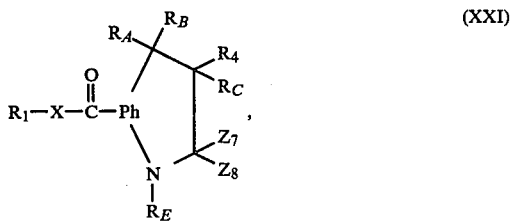

in which $Z_7$ represents a radical that can be converted into optionally etherified hydroxy and $Z_8$ represents a radical $R_D$, or $Z_7$ and $Z_8$ each represents a monovalent, or together represent a divalent, radical that can be converted into oxo, converting $Z_7$ into optionally etherified hydroxy or $Z_7+Z_8$ into oxo, and, if desired, converting the resulting compound into a different compound of the formula I and/or converting a resulting salt-forming compound into a salt or a resulting salt into the free compound or into a different salt.

Radicals that can be converted into optionally etherified hydroxy are, for example, esterified hydroxy groups, optionally etherified mercapto groups or optionally substituted amino groups. Monovalent radicals that can be converted jointly into the oxo group are, for example, esterified hydroxy groups or hydroxy groups etherified by a monohydric open-chain alcohol, or mercapto groups etherified by an open-chain mercaptan. Divalent radicals that can be converted into oxo and that are represented by $Z_7$ and $Z_8$ together are, for example, thioxo, hydroxy groups etherified by a dihydric alcohol, mercapto alcohol or by mercaptan, or optionally substituted imino groups. Esterified hydroxy groups are, for example, hydroxy groups esterified by a mineral acid, an organic sulphonic acid or a carboxylic acid, such as halogen, for example chlorine, bromine or iodine, aliphatic or aromatic sulphonyloxy, for example methane-, ethane-, benzene- or p-toluene-sulphonyloxy, or acyloxy derived from an organic carboxylic acid or a monofunctional carbonic acid derivative, such as a carbonic acid semiester, from a haloformic acid or optionally substituted carbamic acid, for example lower alkanoyloxy, optionally substituted benzoyloxy, lower alkoxycarbonyloxy, optionally substituted phenoxycarbonyloxy, chloro- or bromocarbonyloxy or optionally substituted, such as lower alkylated, carbamoyloxy. Etherified mercapto is, for example, an aliphatic- or aryl-thio group, for example lower alkylthio or optionally substituted phenylthio. Substituted amino is, for example, amino that is mono-substituted by hydroxy or amino mono- or di-substituted by aliphatic radicals or optionally substituted phenyl, it being possible for aliphatic radicals to be mono- or di-valent, monovalent aliphatic radicals being, for example, lower alkyl and divalent aliphatic radicals being, for example, lower alkylene or aza-, oxa- or thia-lower alkylene, for example hydroxyamino, hydrazino, mono- or di-lower alkylamino, optionally substituted anilino, pyrrolidin-1-yl, piperidino, morpholino, thiamorpholino or N'-lower alkylpiperazin-1-yl, such as N'-methylpiperazin-1-yl. Hydroxy etherified by a monohydric alcohol is, for example, lower alkxoy or optionally substituted phenyloxy. Hydroxy groups etherified by a dihydric alcohol are, for example, lower alkylenedioxy or optionally substituted 1,2-phenylenedioxy groups, for example ethylenedioxy, 1,3-propylenedioxy or 1,2-phenylenedioxy. Hydroxy groups etherified by a dihydric mercapto alcohol or mercaptan are, for example, lower alkylenedithio or lower alkyleneoxythio groups or optionally substituted 1,2-phenyldithio or phenoxythio groups, for example ethylenedithio, 1,3-propylenedithio or 1,2-phenylenedithio. Optionally substituted imino groups are, for example, imino groups substituted by hydroxy, amino, lower alkyl or optionally substituted phenyl, for example oximino, hydrazono, lower alkylimino or anilo.

The conversion of the mentioned groups into hydroxy or into oxo is carried out in customary manner, for example by solvolysis, especially hydrolysis. The operation is carried out in customary manner, for example in the presence of an acidic or basic hydrolysis agent and/or a suitable solvent or diluent, if necessary while cooling or heating, for example in a temperature range of approximately from 0° to 100° C., under an inert gas, such as nitrogen, and/or in a closed vessel. Acidic hydrolysis agents are, for example, protonic acids, such as mineral acids, for example hydrochloric, hydrobromic or hydriodic acid, sulphuric acid or phosphoric acid, sulphonic acids, for example methane-, ethane-, benzene- or p-toluene-sulphonic acid, or sulphamic acid, or organic carboxylic acids, such as lower alkanoic acids or optionally substituted benzene acids. Basic hydrolysis agents are, for example, alkali metal hydroxides or carbonates, for example sodium hydroxide or carbonate, potassium hydroxide or carbonate or calcium hydroxide, also nitrogen bases, such as ammonia or organic amines. Suitable solvents or diluents are especially water-miscible solvents.

Reactively esterified hydroxy groups, i.e. hydroxy groups esterified by a hydrohalic acid or an organic sulphonic acid, can also be converted into etherified hydroxy by customary alcoholysis, i.e. reaction with the alcohol corresponding to the desired etherified hydroxy group, for example in the presence of a basic agent, if necessary in a solvent or diluent, while cooling or heating, for example in the temperature range of approximately from 0° to 100° C., under an inert gas, such as nitrogen, and/or in a closed vessel. Suitable basic agents are, for example, alkali metal hydroxides or carbonates, for example sodium hydroxide or carbonate or potassium hydroxide or carbonate, organic, especially tertiary organic, nitrogen bases, such as tri-lower alkylamines, for example triethylamine, or pyridine. Instead of using a basic agent, it is also possible to use the appropriate alcohol advantageously in the form of an alcoholate, such as an alkali metal alcoholate, for example sodium or potassium alcoholate.

The starting materials of the formula XXI, in so far as they are novel, can be obtained according to methods known per se, for example by cyclising a compound of the formula

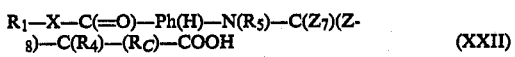

$R_1-X-C(=O)-Ph(H)-N(R_5)-C(Z_7)(Z_8)-C(R_4)-(R_C)-COOH$ (XXII)

or a suitable functional derivative, such as an ester, thereof. The manufacture of compounds of the formula XXII and their cyclisation is carried out especially in the manner indicated for the manufacture and cyclisation of compounds of the formula IV.

Compounds of the formula I in which X represents oxy, and their tautomers, can also be manufactured by, in a compound of the formula XXIII

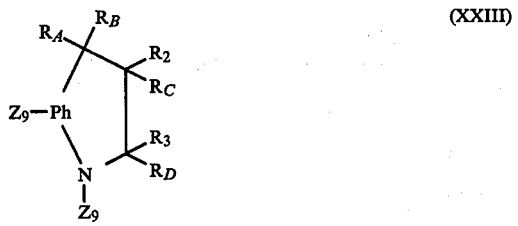

(XXIII)

in which $Z_9$ represents a functionally modified carboxy group other than the group $R_1-X-C(=O)-$, solvolysing $Z_9$ to a corresponding group $R_1-O-C(=O)-$ and, if desired, converting the resulting compound into a different compound of the formula I and/or converting a resulting salt-forming compound into a salt or a resulting salt into the free compound or into a different salt.

Such groups are, for example, cyano, anhydridised carboxy groups, iminoether groups, iminoester groups and etherified and/or esterified trihydroxymethyl groups. Anhydridised carboxy groups are, for example, carboxy groups anhydridised by a mineral acid, such as a hydrohalic acid, by a halosulphonic acid, such as fluorosulphonic acid, or an organic sulphonic or carboxylic acid, such as an aliphatic or aromatic sulphonic or carboxylic acid. Iminoether groups are, for example, iminoether groups derived from esterified carboxy groups $R_1-O-C(=O)-$, such as O-lower alkylcarbamoyl, or cyclic iminoether groups, such as 4,4- or 5,5-di-lower alkyl-, for example 4,4- or 5,5-dimethyl-4,5-dihydrooxazol-2-yl or 4,4,6-tri-lower alkyl-, for example 4,4,6-trimethyl-5,6-dihydrooxazin-2-yl. Iminoester groups are, for example, iminoester groups derived from amidated carboxy groups $R_4$ and esterified by hydrohalic acids or organic carboxylic acids, such as lower alkanoic acids, such as, for example, chlorocarbimino or O-lower alkanoylcarbamoyl. Etherified and/or esterified trihydroxymethyl groups are, for example, tri-lower alkoxymethyl or thihalomethyl groups.

The mentioned groups can be converted by customary hydrolysis into carboxy groups; iminoether groups and etherified hydroxydihalomethyl groups, such as lower alkoxydihalomethyl groups, can similarly be converted into esterified carboxy groups $R_1-O-C(=O)-$. The hydrolysis is carried out in customary manner, for example in the presence of an acidic or alkaline hydrolysis agent, generally in the presence of a solvent and/or diluent or a mixture thereof, and, if necessary, while cooling or heating, for example in a temperature range of from approximately 0° C. to approximately 120° C., if necessary under an inert gas, such as nitrogen, and/or in a closed vessel. Acidic hydrolysis agents are, for example, mineral acids, such as hydrohalic acids, for example hydrochloric acid, or oxygen acids of sulphur or phosphorus, such as sulphuric or phosphoric acid, also organic sulphonic acids, for example p-toluenesulphonic acid or mesitylenesulphonic acid, or organic carboxylic acids, such as lower alkanecarboxylic acids, for example formic or acetic acid. Basic hydrolysis agents are, for example, alkali metal hydroxides, for example sodium or potassium hydroxide, also alkali metal carbonates, for example sodium or potassium carbonate. Suitable solvents or diluents are preferably water-miscible solvents, such as lower alkanols, for example ethanol or methanol, lower ketones, for example acetone, or tertiary alkanoic acid amides, for example dimethylformamide or N-methylpyrrolidone.

Anhydridised carboxy groups and cyclic iminoether groups can also be converted by alcoholysis, i.e. reaction with a corresponding alcohol, into esterified carboxy groups $R_1-O-C(=O)-$. This operation is carried out in customary manner, starting from anhydridised carboxy groups, for example in the presence of a basic condensation agent, such as an alkali metal hydroxide or carbonate, for example sodium or potassium hydroxide or corresponding carbonates, or in the presence of organic nitrogen bases, such as pyridine or triethylamine, and, starting from cyclic iminoether groups, preferably under anhydrous conditions, for example in the presence of hydrogen chloride, phosphoric acid, sulphuric acid or p-toluenesulphonic acid, if necessary while heating, for example in the temperature range of from approximately 0° C. to approximately 150° C., under an inert gas, such as nitrogen, and/or in a closed vessel.

The starting materials of the formula XXIII, in so far as they are novel, can be manufactured according to methods known per se, for example by reaction of a compound of the formula $Z_9-Ph(NH_2)-COOH$ (XXIV) with phosgene to form the isatic acid anhydride, N-substitution of the same and condensation with malonic acid or an ester or anhydride thereof, especially in a manner analogous to that described for the intramolecular condensation of compounds of the formula VI.

The compounds of the formula I can also be manufactured by reacting a compound of the formula XXV

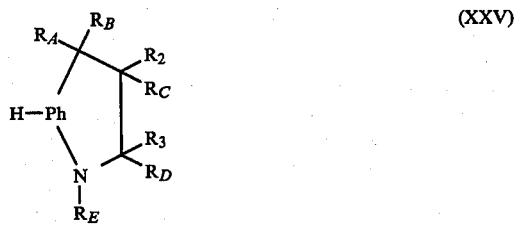

(XXV)

in the presence of a Lewis acid with a compound of the formula $R_1-COOH$ (XXVI) or a suitable functional derivative thereof, and, if desired, converting the resulting compound into a different compound of the formula I and/or converting a resulting salt-forming compound into a salt or a resulting salt into the free compound or into a different salt.

Functional derivatives of acids of the formula XXVI suitable for the above reaction are especially esters or anhydrides of the same, such as lower alkyl esters or optionally substituted phenyl esters, their symmetric anhydrides or their mixed anhydrides with other carboxylic acids, such as formic acid, or especially with mineral acids, such as hydrohalic acids, for example with hydrochloric acid. Lewis acids are, for example, coordinatively unsaturated halides of zinc, boron, aluminium, gallium, tin antimony or iron, such as zinc chloride, boron trichloride or boron trifluoride, aluminium chloride or aluminium bromide, gallium bromide, tin chloride, antimony trichloride or antimony pentachloride or iron trichloride.

The reaction is carried out in the manner known for analogous reactions, for example in a substantially anhydrous solvent that is inert towards the reactants, if necessary while cooling or heating, for example in the temperature range of from −30° to 100° C., under an inert gas, such as nitrogen, and/or in a closed system.

The starting materials of the formula XXV, in so far as they are novel, can be manufactured according to methods known per se, for example by customary cyclisation, for example cyclisation corresponding to the manufacture and intramolecular cyclisation of compounds of the formula VI, of compounds of the formula

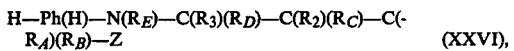

H—Ph(H)—N($R_E$)—C($R_3$)($R_D$)—C($R_2$)($R_C$)—C(-$R_A$)($R_B$)—Z   (XXVI), in which Z represents an etherified or reactively esterified hydroxy group, for example lower alkoxy or halogen.

The compounds of the formula I in which X is a direct bond, can also be manufactured by reacting a compound of the formula XXVII

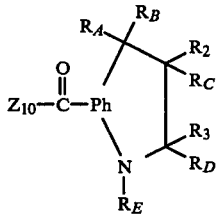

(XXVII)

in which $Z_{10}$ represents a free, etherified or reactively esterified hydroxy group or a suitable heteroaryl group bonded via a ring nitrogen atom, or a salt thereof, with a compound of the formula $R_1$—M (XXVIII) in which M represents a metal radical, to form a compound of the formula (I), wherein $R_1$ differs from hydrogen, or reacting a compound of the formula (XXVII), wherein $Z_{10}$ denotes reactively esterified hydroxy, with bis-(triphenylphosphino)-copper boranate to form a compound of the formula (I), wherein $R_1$ denotes hydrogen, and, if desired, converting the resulting compound into a different compound of the formula I and/or a resulting salt-forming compound into a salt or a resulting salt into the free compound or into a different salt.

Etherified hydroxy groups are, for example, hydroxy groups etherified by an aliphatic alcohol, for example a lower alkanol, or an optionally substituted phenol. Reactively esterified hydroxy groups are especially hydroxy groups esterified by a hydrohalic acid, especially by hydrochloric acid. A heteroaryl radical bonded via a ring nitrogen atoms is, for example, 1-imidazolyl. Metal radicals M are, for example, alkali metal atoms, for example lithium, or magnesium or cadmium radicals, especially of the formula —Mg/2, —Cd/2, —MgHal or —CdHal, in which Hal represents halogen, especially chlorine, bromine or iodine, or copper radicals. Salts of compounds of the formula (XXVII) are, for example, alkali metal salts, such as sodium, potassium or lithium salts, or ammonium salts of the same.

The reaction is carried out in customary manner, especially in the manner known for analogous reactions, preferably in a substantially anhydrous solvent that is inert towards the reactants, if necessary while cooling or while heating gently, for example in the temperature range of from −100° to +80° C., under an inert gas, such as nitrogen, and/or in a closed vessel. Thus, for example, a compound of the formula XXVII in which $Z_9$ represents halogen, can be reacted at temperatures of up to approximately 40° C. with an organo-cadmium compound of the formula XXVIII, or at temperatures below −25° C., preferably below −50° C., with a halomagnesium compound, a lithium compound or especially a copper compound of the formula XXVIII.

A compound of the formula I obtainable according to the invention can be converted in a manner known per se into a different compound of the formula I.

Thus, a compound of the formula I in which $R_1$ is lower alkyl or optionally substituted phenyl can be converted in the manner indicated above into a compound of the formula I in which X represents a direct bond. Furthermore, carboxylic acids of the formula I ($R_1$—X=hydroxy) optionally present in salt form can advantageously be reacted in the temperature range of from appoximately 20° to approximately 50° C., for example in boiling diethyl ether, with a lower alkenyllithium compound. Conversely, a compound of the formula I in which $R_1$ represents a non-aromatic radical can be oxidised in customary manner to a compound of the formula I in which $R_1$—X is hydroxy, for example with an alkali metal hypohalite. In addition, in a compound of the formula I or XIX, carboxy $R_4$ or $R_1$—X—C(=O)— can be converted according to known esterification processes into an esterified carboxy group. Thus, for example, the reaction can be carried out by treatment with an alcohol in the presence of a suitable condensation agent, such as a dehydrating agent, for example dicyclohexyl carbodiimide, or a mineral acid, for example sulphuric acid or hydrochloric acid, or, to form a hydroxy-lower alkyl group, with a corresponding epoxy-lower alkane. The esterification can also be carried out by treatment with a suitable N,N-di-lower alkylformamide acetal, for example N,N-dimethylformamide diethyl acetal, or N,N,O-trimethylformamidinium methosulphate, a carbonate or pyrocarbonate, for example with diethyl(pyro)carbonate, or with an organic sulphite or phosphite, such as a di-lower alkyl sulphite or tri-lower alkyl phosphite, in the last-mentioned case in the presence of a suitable acidic agent, for example p-toluenesulphonic acid. Furthermore, an acid of the formula I to be esterified in which the free carboxy group is in salt form, for example in an alkali metal salt form, such as the sodium salt form, can be reacted with a reactive ester of an alcohol, such as a corresponding halide, for example chloride, bromide or iodide, or with a sulphuric acid ester. It is, however, also possible to carry out the esterification by reaction with a lower alkene corresponding to the lower alkoxy group to be introduced, preferably in the presence of an acidic condensation agent, such as a strong protonic acid, for example sulphuric acid, or a Lewis acid, for example boron trifluoride etherate. Substituents optionally present in one of the esterification reagents mentioned can be in functionally modified form and in that case, in a compound of the formula I in which $R_2$ or $R_3$ represents, for example, substituted lower alkoxycarbonyl in which substituents are in functionally modified form, they can be freed. Thus, there may be used as esterification reagent, for example, the 2,3-epoxypropyl chloride and, in the resulting ester, the 2,3-epoxypropoxy grouping can be subsequently hydrolysed to the desired 2,3-dihydroxypropoxy grouping.

Also, in compounds of the formula I or XIX, esterified carboxy $R_4$ and/or $R_1$—X—C(=O)— can be converted into a different esterified carboxy group by transesterification, for example by treatment with an alcohol, if necessary in the presence of a suitable transesterification catalyst, such as an appropriate alkali metal alcoholate, for example the appropriate sodium or potassium alcoholate, or a mineral acid, for example sulphuric acid or hydrochloric acid.

Moreover, in compounds of the formula I or XIX, free or esterified carboxy $R_4$ can be converted in a manner known per se into optionally substituted carbamoyl. Thus, an ester of the formula I can be treated with ammonia, hydroxylamine or a corresponding primary or secondary amine to obtain amides of the formula I. In addition, the ammonium salt or an amine salt of an acid of the formula I can be converted into an amide of the formula I by dehydration, for example while heating or by the action of a suitable dehydrating agent, such as sulphuric acid.

The conversion of carboxy into esterified or amidated carboxy can, however, alternatively be carried out by converting the carboxy compound first into a reactive carboxy derivative, for example, by reaction with N,N'-bis-(imidazol-1-yl)-urea, into the 1-imidazolide, by reaction with a reactive alcohol, for example with 4-nitrophenol or cyanomethanol, into a reactive ester or by reaction with a halogenating agent, such as thionyl chloride, into the acid chloride, and then reducing with the corresponding alcohol or with ammonia or an amine having at least one hydrogen atom, In compounds of the formula I or XIX, an esterified or amidated carboxy group $R_4$ or $R_1$—X—C(=O)— can be converted in customary manner into the free carboxy group, for example by hydrolysis, generally in the presence of an acidic or basic hyrolysis agent, such as a mineral or carboxylic acid, for example hydrochloric acid, sulphuric acid or acetic acid, or an alkali metal hydroxide or carbonate, for example sodium hydroxide or carbonate or potassium hydroxide or carbonate.

Furthermore, compounds of the formula I or XIX in which $R_A$ and $R_B$ together represent oxo, $R_C$ and $R_D$ together represent an additional bond and $R_E$ represents hydrogen, and their tautomers, can be substituted in customary manner at the nitrogen atom in the 1-position by a radical other than hydrogen and/or they can be etherified at the oxygen atom in the 4-position and/or at a hydroxy group $R_3$. The substitution of the ring nitrogen atom by $R_5$ or the etherification of ring-bonded hydroxy groups is carried out in customary manner, for example by reaction with a reactive ester of a corresponding alcohol, if necessary in the presence of a basic condensation agent, such as an alkali metal hydride, amide, alcoholate or hydroxide, for example sodium hydride, sodium amide, lithium diisopropylamide, sodium methoxide, potassium tert-butoxide or potassium hydroxide, while cooling or heating, for example in the temperature range of approximately from 0° to 120° C., under an inert gas, such as nitrogen and/or in a closed vessel. Reactive esters of corresponding alcohols are especially mineral acid esters, such as hydrohalic or sulphuric acid esters, or organic sulphonic acid esters, for example methane-, ethane-, benzene- p-toluene- or fluoro-sulphonic acid esters. In the case of treatment of an ester of the formula I with an alkyl halide in the presence of sodium hydride in dimethylformamide, when starting from compounds in which $R_2$ is the esterified carboxy group, there are obtained practically exclusively N-alkyl derivatives, while, when starting from compounds of the formula I in which $R_3$ is the esterified carboxy group, there are obtained practically exclusively derivatives alkylated at the oxygen atom in the 4-position.

Moreover, in compound of the formula I of XIX, additional substituents can be introduced into the radical Ph, preferably lower alkyl groups and/or halogen. Thus, for example, lower alkyl can be introduced, especially into the 8-position, by reaction with a lower alkyl halide, a lower alkanol or a lower alkene in the presence of a Lewis acid, for example aluminium trichloride. It is also possible to introduce halogen, again preferably into the 8-position, in customary manner, for example by reaction with the appropriate halogen in the presence of a Lewis acid, such as the corresponding iron halide, which can also be formed in situ from finely divided iron and the appropriate halogen, or by treatment with N-chlorosuccinimide.

Salt-forming compounds of the formula I or XIX can be converted in a manner known per se into salts, for example by treatment with a base or an acid, generally in the presence of a solvent or diluent. Resulting salts can be converted in a manner known per se into the free compounds, for example by treatment with an acidic reagent, such as a mineral acid, or a basic reagent, such as an alkali metal hydroxide. The compounds of the formula I, including their salts, can also be obtained in the form of their hydrates or include the solvent used for crystallisation. Owing to the close relationship between the compounds of the formula I in free form and in the form of their salts, hereinbefore and hereinafter there shall optionally be understood by free compounds and their salts, where appropriate with regard to meaning and purpose, also the corresponding salts and free compounds, respectively.

The invention also relates to those embodiments of the process in which a compound obtainable as an intermediate at any stage of the process is used as the starting material and the remaining process steps are carried out, or a starting material is formed under the reaction conditions or used in the form of a derivative or, optionally, a salt. In the process of the present invention, preferably those starting materials are used that result in the compounds pointed out at the beginning as being especially valuable. The present invention also relates to novel starting materials, analogous processes for their manufacture and their use.

The compounds of the formula I or XIX and their salts have valuable pharmacological properties. They have, especially, antiallergic effects which can be demonstrated, for example, in rats in doses of from approximately 1 mg/kg in the case of intravenous administration and in doses of from approximately 1 mg/kg in the case of oral administration in the passive cutaneous anaphylaxis test (PCA reaction), which is carried out analogously to the method described by Goose and Blair, Immunology, vol. 16, p. 794 (1969). The passive cutaneous anaphylaxis is produced according to the process described by Ovary Progr. Allergy, vol. 5, p. 459 (1958). The antiallergic, especially degranulation-inhibiting, effect of the compounds of the formula I and their salts can also be established in vitro on the basis of histamine release from peritoneal cells of the rat in the dosage range of from approximately 1 to approximately 100 mg/l in the case of immunologically induced release, rats infected with *Nippostrongilus brasiliensis* being used, and from approximately 1.0 to approximately 100 mg/l in the case of chemically induced release, this release being brought about, for example, by a polymer of N-4-methoxyphenylethyl-N-methylamine. The compounds of the present invention can accordingly be used as inhibitors of allergic reactions, for example in the treatment and propylaxis of allergic diseases, such as bronchial asthma both of the extrinsic and intrinsic form, or other allergic diseases, such as allergic rhinitis, for example hay fever, conjunctivitis or allergic dermatides, for example urticaria or eczemas.

As already mentioned, the present invention also relates to pharmaceutical preparations that contain compounds of the formula I or XIX or pharmaceutically acceptable salts of the same. The pharmaceutical preparations according to the invention are those that are intended for enteral, such as oral, nasal or rectal, and also parenteral or buccal, administration to warm-blooded animals and that contain the pharmacological active ingredient alone or together with a pharmaceutically acceptable carrier. The dosage of the active ingredient depends on the species of the warm-blooded animal, age and the individual condition and on the method of administration.

The pharmaceutical preparations according to the invention contain, for example, up to approximately 95%, preferably from approximately 5% to approximately 90%, of the active ingredient. Pharmaceutical preparations according to the invention are, for example, those in dosage unit forms, such as dragées, tablets, capsules, suppositories or ampoules, also inhalation preparations, or topically or locally administrable pharmaceutical preparations, for example for insufflation.

The pharmaceutical preparations of the present invention are manufactured in a manner known per se, for example by means of conventional mixing, granulating, dissolving or lyophilising processes. Thus, pharmaceutical preparations for oral administration can be obtained by combining the active ingredient with solid carriers, optionally granulating the resulting mixture, and processing the mixture or granulate, if desired or necessary after the addition of suitable adjuncts, to form tablets or dragée. cores. Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes, for example, maize, wheat, rice or potato starch paste, gelatin, tragacanth, methylcellulose and/or polyvinylpyrrolidone, and/or, if desired, disintegrating agents, such as the above-mentioned starches, also carboxymethyl starch, cross-linked polyvinylpyrrolidone, agar, alginic acid or a salt thereof, such as sodium alginate. Adjuncts are especially flow-regulating and lubricating agents, for example silica, talc, stearic acid or salts thereof, such as magnesium or calcium stearate, and/or polyethylene glycol. Dragée cores are provided with suitable coatings which are optionally resistant to gastric juices, for which purpose there are used, for example, concentrated sugar solutions, which may contain gum arabic, talc, polyvinylpyrrolidone, polyethylene glycol and/or titanium dioxide, lacquer solutions in suitable organic solvents or solvent mixtures, or, for the manufacture of coatings resistant to gastric juices, solutions of suitable cellulose preparations, such as acetylcellulose phthalate or hydroxypropylmethylcellulose phthalate. Colouring substances or pigments may be added to the tablets or dragée coatings, for example for identification or for distinguishing different doses of the active ingredient. Further orally administrable pharmaceutical preparations are dry-filled capsules made of gelatin, and also soft, sealed capsules made of gelatin and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally with stabilisers. In soft capsules the active ingredient is preferably dissolved or suspended in suitable liquids, such as fatty oils, paraffin oil, or liquid polyethylene glycols, it likewise being possible for stabilisers to be added.

There come into consideration as rectally administrable pharmaceutical preparations, for example, suppositories that consist of a combination of the active ingredient and a suppository base substance. Suitable as a suppository base substance are, for example, natural or synthetic triglycerides, paraffin hydrocarbons, polyethylene glycols or higher alkanols. It is also possible to use gelatin rectal capsules that contain a combination of the active ingredient and a base substance; suitable base substances are, for example, liquid triglycerides, polyethylene glycols or paraffin hydrocarbons.

There are suitable for parenteral administration especially aqueous solutions of the active ingredient in water-soluble form, for example in the form of a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that contain substances that increase viscosity, for example sodium carboxymethylcellulose, sorbitol and/or dextran and optionally stabilisers.

Inhalation preparations for the treatment of the respiratory system by nasal or buccal administration are, for example, aerosols or sprays that can disperse the pharmacological active ingredient in the form of a powder or in the form of drops of a solution or suspension. Preparations having powder-dispersing properties generally contain, apart from the active ingredient, a liquid propellant gas having a boiling point of below room temperature and, if desired, carriers, such as liquid or solid, non-ionic or anionic surface-active agents and/or solid diluents. Preparations in which the pharmacological active ingredient is in solution, contain, in addition, a suitable propellant, and also, if necessary, an additional solvent and/or a stabiliser. Instead of the propellant gas, it is also possible to use compressed air, and this can be produced as required by means of a suitable compression and release device.

Pharmaceutical preparations for topical and local use are, for example, for skin treatment, lotions and cream that contain a liquid or semi-solid oil-in-water or water-in-oil emulsion, and ointments, optionally containing a preservative; for the eyes, eye drops that contain the active compound in aqueous or oily solution, and eye ointments that are preferably manufactured in sterile form; for the treatment of the nose, powders, aerosols and sprays (similar to those described above for the treatment of the respiratory system), and also coarse powders that are administered by rapid inhalation through the nose, and nose drops that contain the active compound in aqueous or oily solution; or for local treatment of the mouth, lozenges that contain the active compound in a composition that is formed generally from sugar and gum arabic or tragacanth and to which flavouring substances may have been added, and also pastilles that contain the active ingredient in an inert composition, for example of gelatin and glycerin or sugar and gum arabic.

The invention relates finally to the use of compounds of the formula I or their salts as pharmacologically active compounds, especially as antiallergic agents, preferably in the form of pharmaceutical preparations. The daily dose administered to a warm-blooded animal weighing approximately 70 kg is, in the case of an oral form of administration, from approximately 100 mg to approximately 1000 mg, preferably from approximately 250 mg to approximately 750 mg.

The following Examples illustrate the invention described above; they are not, however, intended to limit its scope in any way. Temperatures are given in degrees Centigrade.

EXAMPLES

Example 1

17.7 g of 4-amino-2-methylbutyrophenone and 20.2 ml of ethoxymethylenemalonic acid diethyl ester are mixed in a round flask provided with a distillation attachment and heated for 1 hour at 130°. The ethanol released during distillation is distilled off first of all at normal pressure and, after 10 minutes, at reduced pressure. On cooling, the reaction mixture solidifies to a crystalline mass. 100 ml of diphenyl ether are added thereto and the mixture is heated to the boil. Approximately 20 ml of distillate are distilled off and this is cooled, dissolved in approximately 500 ml of hot dimethylformamide, diluted with water, left to crystallise out and filtered with suction. 6-Butyryl-7-methyl-4-oxo-1,4-dihydroquinoline-3-carboxylic acid ethyl ester is obtained.

Example 2

A mixture of 300 ml of ethanol and 100 ml of 2N sodium hydroxide solution is added to 50 g of 6-butyryl-7-methyl-4-oxo-1,4-dihydroquinoline-3-carboxylic acid ethyl ester and the mixture is heated to 70° and maintained at that temperature for 1 hour. The ethanol is removed, the remaining mixture is diluted with water and extracted by shaking with ether, and the aqueous phase is separated off and acidified with concentrated hydrochloric acid. The precipitated crude product is filtered off and recrystallised from ethanol. 6-Butyryl-7-methyl-4-oxo-1,4-dihydroquinoline-3-carboxylic acid having a melting point of 249°–252.5° is obtained.

Example 3

30 g of 6-butyryl-7-methyl-4-oxo-1,4-dihydroquinoline-3-carboxylic acid ethyl ester are dissolved in 1000 ml of dimethylformamide and, in the course of one hour, 4.8 g of a 50% strength sodium hydride dispersion in mineral oil are added in portions. Stirring is carried out for 1 hour at room temperature and then 31.2 g of ethyl iodide are added, and the mixture is then stirred at room temperature for 1 hour, concentrated under reduced pressure, cooled with ice-water and filtered with suction. The product obtained by filtering with suction is dissolved in ethyl acetate, washed with water, dried over sodium sulphate, concentrated and cooled in an ice bath. The precipitated crystallisate is filtered with suction and recrystallised from ethyl acetate. 1-Ethyl-6-butyryl-7-methyl-4-oxo-1,4-dihydroquinoline-3-carboxylic acid ethyl ester having a melting point of 145°–146° is obtained.

Example 4

10 g of 1-ethyl-6-butyryl-7-methyl-4-oxo-1,4-dihydroquinoline-3-carboxylic acid ethyl ester are dissolved in 250 ml of ethanol, 30.4 ml of N sodium hydroxide solution are added and the mixture is stirred for 1 hour at room temperature. The ethanol is removed under reduced pressure, and the aqueous phase is extracted with chloroform and acidified with hydrochloric acid. The precipitated crystallisate is filtered with suction. 1-Ethyl-6-butyryl-7-methyl-4-oxo-1,4-dihydroquinoline-3-carboxylic acid having a melting point of 208°–209° is obtained.

Example 5

17.7 g of 4-amino-2-methylbutyrophenone are dissolved in 200 ml of ethanol, and 17.65 g of acetylenedicarboxylic acid diethyl ester, dissolved in 200 ml of ethanol, are added dropwise thereto. The mixture is stirred for 3 hours at 35° and concentrated to dryness by evaporation under reduced pressure, and the oily residue is chromatographed on a column filled with 550 g of silica gel using first toluene and later a mixture of 9 parts toluene and 1 part chloroform. The eluate is concentrated by evaporation under reduced pressure, 100 ml of diphenyl ether are added and the mixture is heated to 230°–245° in a distillation apparatus. After 5 minutes, approximately 70 ml of diphenyl ether are distilled off under reduced pressure. Petroleum ether is added to the now solid reaction mixture, and the mixture is filtered with suction and the suction filter product is recrystallised from chloroform. 6-Butyryl-7-methyl-4-oxo-1,4-dihydroquinoline-2-carboxylic acid ethyl ester having a melting point of 217°–218° is obtained. By concentrating the petroleum ether solution by evaporation, also 6-butyryl-5-methyl-4-oxo-1,4-dihydroquinoline-2-carboxylic acid ethyl ester having a melting point of 173°–175° is obtained.

Example 6

16.3 g of 6-Butyryl-7-methyl-4-oxo-1,4-dihydroquinoline-2-carboxylic acid ethyl ester are dissolved in 330 ml of dimethylformamide, and 2.6 g of a 50% strength sodium hydride dispersion in mineral oil are added. Stirring is carried out overnight at room temperature and then 8.7 ml of ethyl iodide are added dropwise, and the mixture is stirred for 2 hours at room temperature, concentrated under reduced pressure at 60°, poured onto ice, acidified and filtered with suction. 4-Ethoxy-6-butyryl-7-methylquinoline-2-carboxylic acid ethyl ester having a melting point of 123°–124° is obtained.

Example 7

6 g of 4-ethoxy-6-butyryl-7-methylquinoline-2-carboxylic acid ethyl ester are dissolved in 150 ml of ethanol, 9 ml of 2N sodium hydroxide solution are added and the mixture is hydrolysed for 15 minutes at room temperature. The precipitated crystals are filtered with suction and recrystallised from water. Sodium 4-ethoxy-6-butyryl-7-methylquinoline-2-carboxylate having a melting point of above 250° C. is obtained. By dissolving in water and acidifying, 4-ethoxy-6-butyryl-7-methylquinoline-2-carboxylic acid is obtained.

Example 8

3.9 g of 6-butyryl-5-methyl-4-oxo-1,4-dihydroquinoline-2-carboxylic acid ethyl ester are dissolved in 150 ml of ethanol, 6 ml of 2N-sodium hydroxide solution are added and the mixture is hydrolysed at room temperature for 3 hours. The precipitated sodium 6-butyryl-5-methyl-4-oxo-1,4-dihydroquinoline-2-carboxylate is dissolved in 50 ml of water. The solution is acidified and the precipitated crystals of 6-butyryl-5-methyl-4-oxo-1,4-dihydroquinoline-2-carboxylic acid having a melting point of 237°–238° are filtered with suction and dried.

Example 9

2 g of 6-butyryl-7-methyl-4-oxo-1,4-dihydroquinoline-2-carboxylic acid ethyl ester are heated under reflux for 4 hours together with 20 ml of methanol, 1.2 g of potassium hydroxide and 0.5 ml of water. The reaction mixture is concentrated to dryness by evaporation and taken up in water. The solution is acidified to pH 1 with 2N hydrochloric acid and filtered with suction. The product obtained by filtering with suction is thoroughly washed with water, resuspended in water, thoroughly triturated and stirred at room temperature for 5 hours, then filtered with suction, washed with water, and recrystallised twice from methanol. In this manner 6-butyryl-7-methyl-4-oxo-1,4-dihydroquinoline-2-carboxylic acid having a melting point of 255°–258° is obtained.

Example 10

In a manner analogous to that described in Example 5, N-(2,3-dimethyl-4-butyryl)-2-aminofumaric acid dimethyl ester is obtained from 2,3-dimethyl-4-aminobutyrophenone by the addition of acetylenedicarboxylic acid dimethyl ester in ethanol. This product is heated for 3 hours at 80° in 10 times the amount of polyphosphoric acid and then 80 times the amount of water is added. The reaction mixture is adjusted to pH 7 with solid sodium bicarbonate. Extraction is carried out with ethyl acetate and crude 6-butyryl-7,8-dimethyl-4-oxo-1,4-dihydroquinoline-2-carboxylic acid methyl ester is obtained, which, after recrystallisation from toluene, melts at 157°–159°.

Example 11

6.1 g of 6-butyryl-7,8-dimethyl-4-oxo-1,4-dihydroquinoline-2-carboxylic acid methyl ester are heated under reflux for 4 hours together with 3.66 g of potassium hydroxide, 1.46 ml of water and 64.4 ml of methanol. The reaction mixture is concentrated to dryness by evaporation, partitioned between ethyl acetate and water, the aqueous phases are acidified and the precipitated crystals are filtered with suction and washed with water. The 6-butyryl-7,8-dimethyl-4-oxo-1,4-dihydroquinoline-2-carboxylic acid obtained in this manner melts at 267°–269° after recrystallisation from methanol/ethanol.

Example 12

1.681 g of malonic acid diethyl ester in 25 ml of dimethyl acetamide are cooled to 5° and sodium hydride (0.47 g of a 50% strength suspension in mineral oil, de-oiled with hexane) is added in portions. The internal temperature should not exceed 20° in the course of this addition. Once the exothermic reaction has subsided, stirring is carried out for 15 minutes at room temperature, then the mixture is heated to approximately 100° and, in the course of 60 minutes, 2.628 g of N-ethyl-5-butyryl-4-methylisatic acid anhydride dissolved in 25 ml of dimethylacetamide are added dropwise. The mixture is then heated at 115° for 5 hours, concentrated to dryness by evaporation under reduced pressure, poured into a mixture of 50 ml of ice-water and 10 ml of 2N hydrochloric acid, and stirred until crystallisation occurs. The crystals are filtered with suction, washed with a little diethyl ether, and recrystallised from methanol yielding 1-ethyl-6-butyryl-4-hydroxy-7-methylcarbostyril-3-carboxylic acid ethyl ester having a melting point of 124°–126° C.

The starting material can be produced, for example, in the following manner.

14.6 g of 4-amino-2-methylbutyrophenone are dissolved in 85 ml of acetic acid, 15.07 g of mesoxalic acid diethyl ester are added and the mixture is heated under reflux for 60 minutes. The reaction mixture is concentrated to dryness by evaporation under reduced pressure, and the residue obtained by concentration by evaporation is stirred with 25 ml of diethyl ether, filtered with suction, then washed twice with ice-cold diethyl ether and dried under reduced pressure. 5-Butyryl-3-hydroxy-6-methyloxindole-3-carboxylic acid ethyl ester is obtained. M.p. 180°–181°.

13.0 g of 5-butyryl-3-hydroxy-6-methyloxindole-3-carboxylic acid ethyl ester are suspended in 200 ml of methanol and 85 ml of 2N sodium hydroxide solution are added. The mixture is stirred at room temperature for 90 minutes, the methanol is removed under reduced pressure, the mixture is acidified to pH 3–4 with 2N hydrochloric acid, filtered with suction, then the residue is washed with water, dissolved in ethyl acetate, dried over magnesium sulphate, concentrated to dryness by evaporation under reduced pressure, digested with a little methylene chloride and filtered with suction. 5-Butyryl-4-methylanthranilic acid having a melting point of 184°–186° is obtained.

8.0 g of 5-butyryl-4-methylanthranilic acid are dissolved in 100 ml of dioxan with the addition of 20 ml of 2N hydrochloric acid. Then, while cooling gently at 40°–50°, a weak current of phosgene is introduced for a period of 30 minutes. Subsequently, the solution is concentrated to 30 ml under reduced pressure, filtered with suction, washed twice with a little diethyl ether and dried under reduced pressure. 5-Butyryl-4-methylisatic acid anhydride having a melting point of 224°–226° is obtained.

3.5 g of 5-butyryl-4-methylisatic acid anhydride are dissolved, while heating gently, in 30 ml of hexamethylphosphoric acid triamide, the solution is cooled to 20° and sodium hydride (0.68 g of a 50% strength suspension in mineral oil, de-oiled with hexane) is added. The mixture is stirred until a clear solution is formed and this is cooled to 10°, 2.21 g of ethyl iodide are added, and the mixture is then stirred for 30 minutes at room temperature, poured into a mixture of 300 ml of ice-water and 20 ml of 2N hydrochloric acid, filtered with suction, subsequently washed twice with ice-water, taken up in methylene chloride, dried over magnesium sulphate and concentrated to dryness by evaporation.

N-ethyl-5-butyryl-4-methylisatic acid anhydride having a melting point of 141°–143° is obtained.

Example 13

Analogously to Examples 1–12, or according to one of the methods described in the description, it is also possible to produce the following:
6-butyryl-1,7,8-trimethyl-4-oxo-1,4-dihydroquinoline-2-carboxylic acid ethyl ester,
6-butyryl-1,7,8-trimethyl-4-oxo-1,4-dihydroquinoline-2-carboxylic acid,
6-butyryl-1,7-dimethyl-4-oxo-1,4-dihydroquinoline-3-carboxylic acid ethyl ester, m.p. 184°–186°,
6-butyryl-1,7-dimethyl-4-oxo-1,4-dihydroquinoline-3-carboxylic acid,
6-butyryl-7-methyl-4-oxo-1-propyl-1,4-dihydro-3-quinoline-3-carboxylic acid ethyl ester, m.p. 109°–111°,
1-allyl-6-butyryl-7-methyl-4-oxo-1,4-dihydroquinoline-3-carboxylic acid ethyl ester, m.p. 137°–139°,
6-butyryl-4-hydroxy-1,7-dimethylcarbostyril-3-carboxylic acid ethyl ester, m.p. 130°–131°,
6-butyryl-4-hydroxy-7-methyl-1-propylcarbostyril-3-carboxylic acid ethyl ester, m.p. 116°–117° and
1-allyl-5-butyryl-4-hydroxy-7-methylcarbostyril-3-carboxylic acid ethyl ester, m.p. 112°–114°.

Example 14

2.65 g of malonic acid diethyl ester are dissolved in 40 ml of dimethylacetamide, and the solution is cooled to 10° and converted into the sodium salt with sodium hydride (0.768 g of a 50% strength suspension in mineral oil, de-oiled with hexane) under nitrogen. The sodium salt is heated to 105°, in the course of 1 hour 3.80 g of N-ethyl-5-butyrylisatic acid anhydride in 20 ml of dimethyl acetamide are added dropwise, and the mixture is stirred for 10 hours at 120° and overnight at room temperature. It is then filtered over diatomaceous earth, the dimethyl acetamide is distilled off under reduced pressure, and 250 ml of ice-water and 20 ml of 2N hydrochloric acid are added to the mixture which is then stirred for some time, filtered with suction and dried in the atmosphere. The crude product is recrystallised from methanol/water (90 ml+45 ml), filtered with suction, washed with 50% strength methanol and dried under reduced pressure. 1-Ethyl-6-butyryl-4-hydroxycarbostyril-3-carboxylic acid ethyl ester having a melting point of 163°–165° is obtained.

The starting material can be produced, for example, in the following manner.

81.3 g of acetanilide are suspended in 600 ml of carbon disulphide and 76.7 g of butyryl chloride and, in portions, 198 g of aluminium trichloride are added while stirring. The mixture is stirred for some time at 30°–35° and heated at the boil for 18 hours. It is then allowed to cool, stirred into 200 ml of ice-water and extracted twice with 500 ml of ethyl acetate each time. The organic phases are combined, washed with 500 ml of additional acid and twice with 500 ml of 15% strength sodium carbonate solution each time, dried over magnesium sulphate and concentrated to 150 ml under reduced pressure. The residue obtained by concentration is allowed to cool, filtered with suction, washed twice with diethyl ether and dried under reduced pressure. p-Acetaminobutyrophenone having a melting point of 141°–143° is obtained.

20 g of p-acetaminobutyrophenone are suspended in 40 ml of semi-concentrated hydrochloric acid and the suspension is heated under reflux for 25 minutes and poured into a mixture of 100 ml of ice and 30 ml of concentrated sodium hydroxide solution. The mixture is filtered with suction, then the residue is washed twice with ice-cold water, dried in the atmosphere and recrystallised from methanol/water (20 ml+100 ml). p-Aminobutyrophenone having a melting point of 93°–94° is obtained.

8.15 g of p-aminobutyrophenone are dissolved in 300 ml of methylene chloride and the solution is cooled to −30° under nitrogen. 5.96 g of tert-butyl hypochlorite are then added dropwise and, in the course of this, the mixture is slowly cooled to −65°. Stirring is then carried out for 10 minutes at −65°, 7.37 g of methylthioacetic acid ethyl ester are added dropwise, the mixture is left for one hour at −65°, 5.55 g of triethylamine are added, and the mixture is slowly allowed to warm to room temperature. 100 ml of water are then added, the organic layer is separated off and subsequently washed with 100 ml of water, the aqueous phases are extracted twice with methylene chloride, and the organic phases are combined, dried over magnesium sulphate, filtered and concentrated to dryness by evaporation under reduced pressure. The residue obtained by concentration by evaporation is dissolved in 200 ml of diethyl ether, 25 ml of 2N hydrochloric acid are added and the mixture is stirred overnight at room temperature. The mixture is then diluted with 50 ml of water, the organic phase is separated off, the aqueous phase is washed with 100 ml of diethyl ether, the organic phases are combined, washed with a mixture of 50 ml of water and 10 ml of 2N hydrochloric acid, dried over magnesium sulphate and concentrated to dryness by evaporation, and the residue is suspended in diethyl ether, filtered with suction and dried under reduced pressure. 5-Butyryl-3-methylthiooxindole having a melting point of 133°–136° is obtained.

1.10 g of potassium hydroxide are added to 1.50 g of 5-butyryl-3-methylthiooxindole in 50 ml of tetrahydrofuran and the mixture is stirred intensively for 3 hours in a stream of air. The mixture is acidified to pH 1 with 2N hydrochloric acid, the tetrahydrofuran is distilled off under reduced pressure, 10 ml of 2N sodium hydroxide solution are added, 0.5 ml of 30% strength hydrogen peroxide is added while stirring, and the mixture is stirred at room temperature for 15 minutes, acidified to pH 1 with 2N hydrochloric acid, filtered with suction and left to dry in the atmosphere. The crude product is dissolved in aqueous potassium carbonate solution, clarified with activated carbon, filtered, acidified again with 2N hydrochloric acid to pH 1, filtered with suction and dried under reduced pressure. 5-Butyrylanthranilic acid (2-amino-5-butyrylbenzoic acid) having a melting point of 195°–197° is obtained.

Into a solution of 4.4 g of the 5-butyrylanthranilic acid in 60 ml of dioxan and 20 ml of 2N hydrochloric acid, phosgene is cautiously introduced with external cooling (strong exothermic reaction!) until the exothermic reaction has subsided (approximately 90 minutes). The mixture is filtered with suction, washed twice in each case with water and diethyl ether and dried under reduced pressure. 5-Butylisatic acid anhydride having a melting point of 218°–220° is obtained.

4.00 g of the anhydride are dissolved in 35 ml of hexamethylphosphoric acid triamide, the solution is cooled to 5° and sodium hydride (0.864 g of a 50% strength suspension in mineral oil, de-oiled with hexane) is added under nitrogen. The mixture is allowed to warm to room temperature, 2.8 g of ethyl iodide are added and stirring is then carried out for 1 hour first at room temperature, then at 40°, and the reaction mixture is poured into a mixture of 300 ml of ice-water and 20 ml of 2N hydrochloric acid, filtered with suction, washed with water and allowed to dry in the atmosphere. N-Ethyl-5-butylisatic acid anhydride having a melting point of 130°–132° is obtained.

Example 15

3.8 g of malonic acid di-tert-butyl ester are dissolved in 40 ml of dimethyl acetamide and converted into the sodium salt by treating with sodium hydride (0.843 g of a 50% strength suspension in mineral oil, de-oiled with hexane). The sodium salt is heated to 105° and, in the course of 1 hour, a solution of N-ethyl-5-butyryl-4-methylisatic acid anhydride in 30 ml of dimethyl acetamide is added. The mixture is stirred at 120° for 5 hours, the dimethyl acetamide is substantially distilled off under reduced pressure, 100 ml of ice-water are added and the reaction mixture is poured into a mixture of 10 ml of 2N hydrochloric acid and 200 ml of ice-water. The crystalline precipitate is filtered with suction, washed twice with cold water and taken up in methylene chloride. The organic phase is separated off, dried over magnesium sulphate, filtered and concentrated by evaporation. The crude product is dissolved in 20 ml of a mixture of 3 parts toluene and 1 part ethyl acetate and chromatographed over 60 g of silica gel using the above solvent mixture as eluant. 30 ml fractions are collected. Fractions 3–9, which according to the thin layer chromatogram contain the desired product, are combined, concentrated by evaporation and recrystallised from 15 ml of methanol. 1-Ethyl-6-butyryl-4-hydroxy-7-methylcarbostyril-3-carboxylic acid tert-butyl ester having a melting point of 124°–126° is obtained.

Example 16

7.13 g of 1-ethyl-6-butyryl-4-hydroxy-7-methylcarbostyril-3-carboxylic acid tert-butyl ester are suspended in 100 ml of diethyl ether and, while stirring, 2.0 ml of 70% strength perchloric acid are carefully added. The reaction mixture is stirred for 10 minutes at 30°, cooled by means of an ice bath and suction-filtered and the residue is washed twice with a little diethyl ether and subsequently with hexane, then allowed to dry at room temperature. In this manner 1-ethyl-6-butyryl-4-hydroxy-7-methylcarbostyril-3-carboxylic acid having a melting point of 157°–158° is obtained.

Example 17

3.64 g of malonic acid diethyl ester are dissolved in 50 ml of dimethyl acetamide and converted into the sodium salt in the cold, under nitrogen, with sodium hydride (1.09 g of a 50% strength suspension in mineral oil, de-oiled with hexane). The sodium salt is then heated to 105°, in the course of 1 hour 5.95 g of N-allyl-5-butyryl-4-methylisatic acid anhydride in 30 ml of dimethyl acetamide are added dropwise, and the mixture is stirred for 9 hours at 120° and overnight at room temperature. The dimethyl acetamide is then substantially distilled off under reduced pressure. Approximately 100 g of ice and 20 ml of 2N hydrochloric acid are added to the reaction mixture while stirring and the precipitated crystals are filtered with suction, then washed with cold diethyl ether, dried under reduced pressure and recrystallised from approximately 30 ml of methanol. 1-Allyl-6-butyryl-4-hydroxy-7-methylcarbostyril-3-carboxylic acid ethyl ester having a melting point of 112°–114° is obtained.

The starting material can be produced by reacting 5-butyryl-4-methylisatic acid anhydride with allyl bromide in a manner analogous to that described in Example 12.

Example 18

3.95 g of malonic acid diethyl ester are dissolved in 50 ml of dimethyl acetamide and converted into the sodium salt with sodium hydride (1.07 g of a 50% strength suspension in mineral oil, de-oiled with hexane). The sodium salt is heated to 105°, in the course of 90 minutes 6.20 g of N-butyl-5-butyryl-4-methylisatic acid anhydride in 30 ml of dimethyl acetamide are added dropwise and the mixture is stirred for 10 hours at 120° and overnight at room temperature. The dimethyl acetamide is then distilled off, 200 ml of ice-water and 20 ml of 2N hydrochloric acid are added to the reaction mixture and this is stirred intensively for some time and filtered with suction, and the residue is then washed twice with ice-water and dried in the atmosphere. The crude product is purified by chromatography over 60 g of silica gel with toluene/ethyl acetate (9:1) as eluant. The product is concentrated by evaporation, digested with 30 ml of diethyl ether and then with 50 ml of hexane, filtered with suction, subsequently washed with hexane and dried under reduced pressure. 1-Butyl-6-butyryl-4-hydroxy-7-methylcarbostyril-3-carboxylic acid ethyl ester having a melting point of 104°–105° is obtained.

The starting material can be produced by reacting 5-butyryl-4-methylisatic acid anhydride with butyl iodide in the manner described in Example 12.

Example 19

2.98 g of malonic acid diethyl ester are dissolved in 50 ml of dimethyl acetamide and converted into the sodium salt with sodium hydride (0.895 g of a 50% strength suspension in mineral oil, de-oiled with hexane). The sodium salt is heated to 105°, in the course of 1 hour 4.9 g of 5-butyryl-4-methyl-N-propylisatic acid anhydride in 30 ml of dimethyl acetamide are added dropwise thereto, and the mixture is heated for 10 hours at 120° and stirred overnight at room temperature. The dimethyl acetamide is distilled off under reduced pressure, 200 g of ice and 20 ml of 2N hydrochloric acid are added and the reaction mixture is stirred intensively for a short time. The crystalline precipitate is filtered with suction, washed twice with ice-water, dried, suspended in diethyl ether, filtered with suction again and washed with diethyl ether. The crude product is purified by chromatography over 60 g of silica gel with toluene as eluant. The eluate is concentrated by evaporation under reduced pressure, suspended in diethyl ether, filtered with suction, washed with cold diethyl ether and dried. 6-Butyryl-4-hydroxy-7-methyl-1-propylcarbostyril-3-carboxylic acid ethyl ester having a melting point of 116°–117° is obtained.

The starting material is obtained by reacting 5-butyryl-4-methylisatic acid anhydride as described in Example 12.

Example 20

2.6 g of a sodium hydride-mineral oil dispersion (60% strength) are added in portions at room temperature, while stirring and with the introduction of nitrogen gas, to a solution of 6.1 g of malonic acid diethyl ester in 210 ml of anhydrous dimethylformamide. The mixture is stirred for 30 minutes at room temperature and 30 minutes at 120° and cooled to room temperature, and a solution of 14.0 g of N-allyl-5-methoxycarbonylisatic acid anhydride in 140 ml of anhydrous dimethylformamide is added. The reaction mixture is then stirred for 4 hours at 120°, cooled and concentrated to dryness by evaporation at 0.13 mbar and 60°. 350 ml of water are added to the residue and extraction is carried out twice with 120 ml of methylene chloride each time. The aqueous phase is acidified at 0° with 2N hydrochloric acid. The separated oil is extracted three times with 170 ml of methylene chloride each time. The combined organic phases are washed with 50 ml of water, dried over magnesium sulphate and concentrated to dryness by evaporation under reduced pressure. The residue is then crystallised from methylene chloride/petroleum ether. 1-Allyl-6-methoxycarbonyl-4-hydroxycarbostyril-3-carboxylic acid ethyl ester having a melting point of 123°–125° is obtained.

In an analogous manner it is possible starting from N-ethyl- and N-propargyl-5-methoxycarbonylisatic acid anhydride, respectively, and malonic acid diethyl ester, also to produce 1-ethyl-6-methoxycarbonyl-4-hydroxycarbostyril-3-carboxylic acid ethyl ester, m.p. 178°–180° (from methylene chloride/petroleum ether) and 4-hydroxy-6-methoxycarbonyl-1-propargylcarbostyril-3-carboxylic acid ethyl ester, respectively.

The starting material can be produced, for example, in the following manner.

100 ml of 2N hydrochloric acid are added, while stirring, to a solution of 34.5 g of 5-methoxycarbonylanthranilic acid in 200 ml of dioxan. Phosgene gas is introduced into the suspension at 40°, while stirring, and first of all a solution forms and then crystals precipitate out. After introducing phosgene for 2 hours, the mixture is cooled to 5° and filtered. The crystals are washed with 50 ml of water, dried under reduced pressure, suspended in 200 ml of ether, filtered and dried for 15 minutes at 50° and 0.13 mbar. 5-Methoxycarbonylisatic acid anhydride having a melting point of 256°–257° is obtained.

A solution of 20.0 g of 5-methoxycarbonylisatic acid anhydride in 630 ml of anhydrous dimethylformamide is added dropwise, while stirring and with the introduction of nitrogen, to a suspension of 4.33 g of sodium hydride-mineral oil dispersion (60% strength) in 180 ml of anhydrous dimethylformamide. The mixture is stirred at room temperature for 15 minutes and a solution of 23.2 g of allyl bromide in 130 ml of anhydrous dimethylformamide is added. The reaction mixture is stirred at room temperature for 20 hours, concentrated to 300 ml at 0.13 mbar and 50°, and the residue is poured into 2000 ml of ice-water. The precipitated crystals are extracted three times with 500 ml of diethyl ether each time. The combined ether extracts are washed with 200 ml of water, dried over magnesium sulphate and concentrated to dryness by evaporation under reduced pressure. The residue is crystallised first from diethyl ether/petroleum ether and then from tetrahydrofuran/n-hexane. The N-allyl-5-methoxycarbonylisatic acid anhydride melts at 116°–118°.

The following are produced analogously: N-ethyl-5-methoxycarbonylisatic acid anhydride, m.p. 145°–147° (from tetrahydrofuran/n-hexane) and 5-methoxycarbonyl-N-propargylisatic acid anhydride (by reaction with ethyl bromide and propargyl bromide respectively).

Example 21

A solution of 3.3 g of 1-allyl-6-methoxycarbonyl-4-hydroxycarbostyril-3-carboxylic acid ethyl ester in 20.0 ml of N sodium hydroxide solution is stirred at room temperature for 15 hours, extracted with 10.0 ml of diethyl ether and acidified with hydrochloric acid. The precipitated crystals are filtered off and recrystallised from methanol. The resulting 1-allyl-6-carboxy-4-hydroxycarbostyril-3-carboxylic acid ethyl ester melts above 280°.

In an analogous manner, 1-ethyl-6-carboxy-4-hydroxycarbostyril-3-carboxylic acid ethyl ester, m.p. >280° (from methanol) can be produced starting from 1-ethyl-6-methoxycarbonyl-4-hydroxycarbostyril-3-carboxylic acid ethyl ester.

Example 22

A solution of 4.45 g of N-allyl-5-methoxycarbonylisatic acid anhydride in 400 ml of anhydrous dimethylformamide is added, while stirring, to a solution of 7.0 g of the sodium salt of formylacetic acid ethyl ester in 600 ml of anhydrous dimethylformamide. While introducing nitrogen, the mixture is stirred for 4 hours at 110° and then concentrated to dryness by evaporation under reduced pressure at 70°. 40 ml of water are added to the residue and extraction is carried out three times with 70 ml of diethyl ether each time. The combined ether phases are dried over magnesium sulphate and concentrated to dryness by evaporation under reduced pressure. The residue is crystallised from methylene chloride-n-hexane. 1-allyl-6-methoxycarbonyl-4-oxo-1,4-dihydroquinoline-3-carboxylic acid ethyl ester having a melting point of 156°–163° is obtained.

Example 23

3.66 g of formylacetic acid ethyl ester are converted into the sodium salt in 75 ml of dimethyl acetamide with sodium hydride (1.41 g of a 50% strength suspension in mineral oil, de-oiled with hexane). 6.08 g of N-ethyl-5-butyryl-4-methylisatic acid anhydride in 75 ml of dimethyl acetamide are added, the reaction mixture is heated at 110° for 4 hours, concentrated to 50 ml under reduced pressure, 200 ml of ice-water and 30 ml of 2N hydrochloric acid are added, the mixture is suction-filtered, and the residue is subsequently washed with a little cold diethyl ether and recrystallised twice from methanol. 1-Ethyl-6-butyryl-7-methyl-4-oxo-1,4-dihydroquinoline-3-carboxylic acid ethyl ester having a melting point of 145°–146° is obtained.

Example 24

1.4 g of 1-ethyl-6-butyryl-4-hydroxy-7-methylcarbostyril-3-carboxylic acid nitrile are heated under reflux overnight in 50 ml of 96% strength ethanol and 10 g of anhydrous ammonium chloride. The mixture is filtered, and the residue is concentrated to dryness by evaporation under reduced pressure and recrystallised from 50% strength methanol. 1-Ethyl-6-butyryl-4-hydroxy-7-methylcarbostyril-3-carboxylic acid ethyl ester having a melting point of 125°–126° is obtained.

The starting material can be obtained in a manner analogous to that described in Example 12 by reacting cyanoacetic acid ethyl ester/sodium hydride with N-ethyl-5-butyryl-4-methylisatic acid anhydride.

Example 25

Analogously to Examples 1–24 it is possible furthermore to produce the following:
6-ethoxycarbonyl-1-ethyl-4-hydroxycarbostyril-3-carboxylic acid ethyl ester,
1-ethyl-6-pivaloyloxymethoxycarbonyl-4-hydroxycarbostyril-3-carboxylic acid ethyl ester,
1-ethyl-6-[2-(2-hydroxyethoxy)-ethoxycarbonyl]-4-hydroxycarbostyril-3-carboxylic acid ethyl ester,
1-ethyl-6-{2-[2-(2-methoxyethoxy)-ethoxy]-ethoxycarbonyl}-4-hydroxycarbostyril-3-carboxylic acid ethyl ester,
1-ethyl-6-{2-[2-(2-hydroxyethoxy)-ethoxy]-ethoxycarbonyl}-4-hydroxycarbostyril-3-carboxylic acid ethyl ester and 6-ethoxycarbonyl-1-ethyl-4-hydroxycarbostyril-3-carboxylic acid tert-butyl ester.

The higher esters of N-ethyl-5-carboxyisatic acid anhydride to be used as starting materials can be obtained starting from the methyl ester by transesterification or hydrolysis by means of sodium hydroxide solution to the acid as well as esterification of the same with the relevant alcohol in the presence of dicyclohexyl carbodiimide and 4-dimethylaminopyridine in tetrahydrofuran as solvent.

Example 26

19.6 g of N-ethyl-5-butyryl-4-methyl-N-(1'-oxo-2'-ethoxycarbonylethyl)-anthranilic acid ethyl ester in 60 ml of absolute ethanol are added dropwise, at room temperature, to a solution of 1.15 g of sodium in 30 ml of absolute ethanol. The yellow solution is refluxed for 3 hours. The resulting suspension is then freed of ethanol in vacuo. The residue is dissolved in ice-water and acidified with hydrochloric acid. The separated oil is extracted with methylene chloride and the methylene chloride solution is washed with water, dried over sodium sulphate, filtered and concentrated to dryness by evaporation in vacuo. An oil is obtained, which is caused to crystallise from methanol. In this manner 1-ethyl-6-butyryl-4-hydroxy-7-methylcarbostyril-3-carboxylic acid ethyl ester having a melting point of 124°–126° is obtained.

The N-ethyl-5-butyryl-4-methyl-N-(1'-oxo-2'-ethoxycarbonylethyl)-anthranilic acid ethyl ester required as starting material can be obtained in the following manner.

2.3 g of sodium are dissolved in 250 ml of ethanol. There are added to this solution 27.5 g of N-ethyl-5-butyryl-4-methylisatic acid anhydride suspended in 300 ml of ethanol. The mixture is refluxed for 1 hour. The solution is concentrated to dryness by evaporation and ice-water is added and acidification with 2N HCl is cautiously carried out. The mixture is then extracted with methylene chloride, dried over magnesium sulphate and concentrated by evaporation. The N-ethyl-5-butyryl-4-methylanthranilic acid ethyl ester obtained in this manner is further reacted in the following manner without being purified.

13.86 g of the above anthranilic acid ethyl ester are dissolved in 140 ml of absolute toluene and 6.45 g of ethyl diisopropylamine are added. A solution of 7.6 g of chlorocarbonylacetic acid ethyl ester in 75 ml of absolute toluene is added dropwise at room temperature to this solution over a period of 30 minutes. After stirring for 10 hours at room temperature, a further 7.6 g of chlorocarbonylacetic acid ethyl ester in toluene are added dropwise in the course of 15 minutes and the mixture is stirred for a further 15 hours at room temperature. The reaction mixture is washed with water, sodium bicarbonate solution and water, dried over anhydrous sodium sulphate, filtered and concentrated to dryness by evaporation in vacuo. In this manner N-ethyl-5-butyryl-4-methyl-N-(1'-oxo-2'-ethoxycarbonylethyl)-anthranilic acid ethyl ester is obtained in the form of a pale yellow oil, which is further processed without further purification.

Example 27

10.1 g of 1-ethyl-4-hydroxy-6-carboxycarbostyril-3-carboxylic acid ethyl ester are dissolved in 100 ml of pyridine and stirred for 2 hours at room temperature with 2.4 ml of thionyl chloride. The dark solution is then concentrated to dryness by evaporation, two 30 ml portions of toluene are added and concentration by evaporation is carried out again. The resulting acid chloride is dissolved in 100 ml of absolute tetrahydrofuran, the solution is filtered and, at −20°, added dropwise to a solution of propyl lithium in diethyl ether. The mixture is stirred for 30 minutes at −20° and is then stirred for 2 hours at room temperature. With external cooling, a saturated aqueous ammonium chloride solution is then added dropwise and the organic layer is separated off and dried over sodium sulphate. The filtered-off solution is concentrated to dryness by evaporation. The crude material is chromatographed over 200 g of silica gel. 1-Ethyl-5-butyryl-4-hydroxycarbostyril-3-carboxylic acid ethyl ester having a melting point of 163°–165° is eluted with toluene/ethyl acetate 1:1.

Example 28

A 2% aqueous solution of sodium 4-ethoxy-6-butyryl-7-methylquinoline-2-carboxylate suitable for inhalation can be produced as follows:

|  | Composition (for 100 ml): |
|---|---|
| sodium 4-ethoxy-6-butyryl-7-methylquinoline-2-carboxylate | 2.000 g |
| disodium salt of ethylenediaminetetraacetic acid (stabiliser) | 0.010 g |
| benzalkonium chloride (preservative) | 0.010 g |
| water, distilled | ad 100 ml |

The sodium 4-ethoxy-6-butyryl-7-methylquinoline-2-carboxylate is dissolved in freshly distilled water and there is added to the solution the disodium salt of ethylenediaminetetraacetic acid and the benzalkonium chloride, that is a mixture of alkyl-methyl-benzylammonium chlorides, in which alkyl contains from 8 to 18 carbon atoms. Once the components have dissolved completely, the resulting solution is made up to a volume of 100 ml with water, filled into containers and sealed gas-tight.

Example 29

Capsules suitable for insufflation containing 0.025 g of 1-ethyl-6-butyryl-4-hydroxy-7-methylcarbostyril-3-carboxylic acid ethyl ester can be produced as follows:

| Composition (for 1000 capsules) | |
|---|---|
| 1-ethyl-6-butyryl-4-hydroxy-7-methoxycarbostyril-3-carboxylic acid ethyl ester (active ingredient) | 25.00 g |

-continued

| Composition (for 1000 capsules) | |
|---|---|
| lactose, ground | 25.00 g |

The active ingredient and the lactose (very finely ground) are mixed thoroughly with each other. The resulting powder is sieved and filled in portions of 0.05 g each into gelatin capsules.

Example 30

Tablets containing 100 mg of 1-ethyl-6-butyryl-4-hydroxy-7-methylcarbostyril-3-carboxylic acid ethyl ester as active ingredient can be produced, for example, in the following composition.

| Composition | per tablet |
|---|---|
| active ingredient | 100 mg |
| lactose | 50 mg |
| wheat starch | 73 mg |
| colloidal silica | 13 mg |
| talc | 12 mg |
| magnesium stearate | 2 mg |
| | 250 mg |

Manufacture

The active ingredient is mixed with the lactose, a portion of the wheat starch and with the colloidal silica, and the mixture is forced through a sieve. A further portion of the wheat starch is made into a paste with 5 times the amount of water on a water bath and the pulverulent mixture is kneaded with this paste until a weakly plastic mass is obtained. This mass is forced through a sieve having a mesh width of approximately 1 mm and dried, and the dry granules are forced through a sieve again. The remainder of the wheat starch, the talc and the magnesium stearate are then admixed. The resulting tabletting mixture is pressed into tablets each weighing 250 mg and having one or more breaking notches.

Example 31

Analogously to Examples 28 to 30 it is also possible to produce pharmaceutical preparations containing another compound according to any one of Examples 1-27.

We claim:

1. A compound of the formula

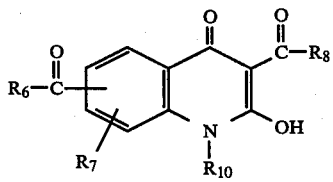

in which $R_6$ represents lower alkyl having 3 to 5 carbon atoms; $R_7$ represents hydrogen or lower alkyl having up to and including 4 carbon atoms, lower alkoxy having up to and including 4 carbon atoms, halogen having an atomic number of up to and including 35, or hydroxy; $R_8$ represents hydroxy or lower alkoxy having up to 4 carbon atoms; and $R_{10}$ represents lower alkyl, lower alkenyl or lower alkynyl having up to 4 carbon atoms, it also being possible for the 2 hydroxy-4-oxo-1,4-dihydroquinoline structure of the formula to be in the tautomeric 2-oxo-4-hydroxy-1,2-dihydro- or 2,4-dioxo-1,2,3,4-tetrahydroquinoline form, or a salt thereof.

2. A compound according to claim 1 in which the group $R_6$—C(=O)— is in the 6-position and the lower alkyl group $R_7$ is in the 7-position.

3. A compound as claimed in claim 1 being 6-butyryl-4-hydroxy-1,7-dimethylcarbostyril-3-carboxyclic acid ethyl ester.

4. A compound as claimed in claim 1 being 6-butyryl-4-hydroxy-7-methyl-1-propylcarbostyril-3-carboxylic acid ethyl ester.

5. A compound as claimed in claim 1 being 1-ethyl-6-butryl-4-hydroxy-7-methylcarbostyril-3-carboxylic acid ethyl ester.

6. A compound as claimed in claim 1 being 1-allyl-6-butyryl-4-hydroxy-7-methylcarbostyril-3-carboxylic acid ethyl ester.

7. A compound as claimed in claim 1 being 1-ethyl-6-butyryl-4-hydroxycarbostyril-3-carboxylic acid ethyl ester.

8. A compound as claimed in claim 1 being 1-butyl-6-butyryl-4-hydroxy-7-methylcarbostyril-3-carboxylic acid ethyl ester.

9. 1-ethyl-6-butyryl-4-hydroxy-7-methylcarbostyril-3-carboxylic acid.

10. A antiallergic preparation comprising an effective amount of one or more than one compound according to claim 1 in the free form or in the form of a pharmaceutically acceptable salt in addition to customary pharmaceutical adjuncts and carriers.

11. A method for inhibiting allergic reactions comprising administering to a warm blooded animal in need of such administration an effective amount of a compound of the following formula

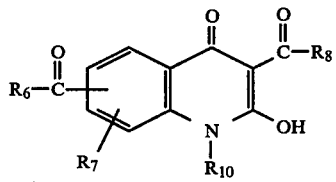

in which $R_6$ represents lower alkyl having 3 to 5 carbon atoms; $R_7$ represents hydrogen or lower alkyl having up to and including 4 carbon atoms, lower alkoxy having up to and including 4 carbon atoms, halogen having an atomic number of up to and including 35, or hydroxy; $R_8$ represents hydroxy or lower alkoxy having up to 4 carbon atoms; and $R_{10}$ represents lower alkyl, lower alkenyl or lower alkynyl having up to 4 carbon atoms, it also being possible for the 2 hydroxy-4-oxo-1,4-dihydroquinoline structure of the formula to be in the tautomeric 2-oxo-4-hydroxy-1,2-dihydro- or 2,4-dioxo-1,2,3,4-tetrahydroquinoline form, or a salt thereof.

12. A compound as claimed in claim 1 being 1-ethyl-6-butyryl-4-hydroxy-7-methylcarbostyril-3-carboxylic acid tert-butyl ester.

* * * * *